(12) United States Patent
Tojo et al.

(10) Patent No.: US 9,124,939 B2
(45) Date of Patent: Sep. 1, 2015

(54) IMAGE OUTPUT APPARATUS, MEASUREMENT ASSISTANCE SYSTEM, IMAGE OUTPUT CONTROLLER, AND IMAGE OUTPUTTING METHOD

(71) Applicant: Panasonic Corporation, Osaka (JP)

(72) Inventors: Tomoaki Tojo, Hyogo (JP); Koji Hirose, Osaka (JP); Nobuhiko Okamoto, Nara (JP); Haruyuki Shimizu, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 30 days.

(21) Appl. No.: 14/079,717

(22) Filed: Nov. 14, 2013

(65) Prior Publication Data
US 2014/0143805 A1    May 22, 2014

(30) Foreign Application Priority Data
Nov. 20, 2012    (JP) ................................. 2012-253982

(51) Int. Cl.
| | | |
|---|---|---|
| H04N 1/44 | (2006.01) | |
| H04N 21/488 | (2011.01) | |
| H04N 21/81 | (2011.01) | |
| H04N 21/45 | (2011.01) | |
| H04N 7/16 | (2011.01) | |
| G06F 19/00 | (2011.01) | |
| G06Q 50/22 | (2012.01) | |
| H04N 21/41 | (2011.01) | |
| H04N 21/422 | (2011.01) | |

(52) U.S. Cl.
CPC ........ *H04N 21/4882* (2013.01); *G06F 19/3418* (2013.01); *G06Q 50/22* (2013.01); *H04N 1/4406* (2013.01); *H04N 1/4433* (2013.01); *H04N 7/163* (2013.01); *H04N 21/4131* (2013.01); *H04N 21/42201* (2013.01); *H04N 21/4532* (2013.01); *H04N 21/8146* (2013.01)

(58) Field of Classification Search
CPC ... H04N 1/4406; H04N 1/4433; H04N 7/163; H04N 21/4532
See application file for complete search history.

(56) References Cited

U.S. PATENT DOCUMENTS

| | | | | |
|---|---|---|---|---|
| 5,434,611 A | * | 7/1995 | Tamura .......................... | 725/116 |
| 5,987,519 A | * | 11/1999 | Peifer et al. ................... | 709/230 |
| 6,988,075 B1 | * | 1/2006 | Hacker ............................ | 705/3 |
| 7,185,282 B1 | * | 2/2007 | Naidoo et al. ................ | 715/718 |
| 2013/0226604 A1 | * | 8/2013 | Etchegoyen ..................... | 705/2 |

FOREIGN PATENT DOCUMENTS

JP    2002-366652    12/2002

* cited by examiner

*Primary Examiner* — Robert Hance
(74) *Attorney, Agent, or Firm* — Wenderoth, Lind & Ponack, L.L.P.

(57) ABSTRACT

The image output apparatus includes an output unit that outputs content data indicating video content, and a control unit that controls the output unit to cause the output unit to output image data instead of or together with the content data when the output unit is outputting the content data. The image data is for prompting a user to measure to obtain the body information indicating a body condition of the user using an external apparatus.

12 Claims, 14 Drawing Sheets

IMAGE OUTPUT APPARATUS, MEASUREMENT ASSISTANCE SYSTEM, IMAGE OUTPUT CONTROLLER, AND IMAGE OUTPUTTING METHOD

CROSS REFERENCE TO RELATED APPLICATION

The present application is based on and claims priority of Japanese Patent Application No. 2012-253982 filed on Nov. 20, 2012. The entire disclosure of the above-identified application, including the specification, drawings and claims is incorporated herein by reference in its entirety.

FIELD

The techniques disclosed herein relate to an image output apparatus, a measurement assistance system, an image output controller, and an image outputting method.

BACKGROUND

Patent Literature 1 discloses a medical information communication system. The medical information communication system includes a terminal for a patient, a terminal for a doctor, and a server provided between the terminal for a patient and the terminal for a doctor. The terminal for a patient is connected to the terminal for a doctor and the server via a network.

When the time for a patient to measure to obtain biological information has come, the terminal for a patient uses a text, an image, a sound, a speech, or the like and prompts the patient to measure to obtain the biological information. The server stores the information on the time for the patient to measure to obtain the biological information. The server calculates the difference between the time when the server receives the biological information of the patient from the terminal for a patient and the time for the patient to measure to obtain the biological information. When the calculated difference is large, the server notifies the terminal for a doctor of an inadequacy in the measurement to obtain the biological information by the patient. The terminal for a patient may be a television.

Thus, the doctor that has the terminal for a doctor can know the inadequacy in the measurement to obtain the biological information by the patient without asking the patient directly.

CITATION LIST

Patent Literature

[Patent Literature 1] Japanese Unexamined Patent Application Publication No. 2002-366652

SUMMARY

As described above, in the medical information communication system disclosed in Patent Literature 1, the terminal for a patient uses a text, an image, a sound, a speech, or the like and prompts the patient to measure to obtain the biological information when the time for the patient to measure to obtain the biological information has come. According to Patent Literature 1, the terminal for a patient may be a television.

However, in Patent Literature 1, the patient does not measure to obtain the biological information in some cases even if the terminal for a patient prompts the patient to measure to obtain the biological information. For example, when the patient is watching a broadcasting program and a text, an image, a sound, a speech, or the like is presented to the patient for prompting of the measurement, the patient may neglect the prompting, and may not measure to obtain the biological information.

Then, the present disclosure provides an image output apparatus, measurement assistance system, image output controller, and image outputting method that can prompt a user to measure to obtain body information when the user is watching video content.

To solve the problem above, an image output apparatus according to one aspect of the present disclosure includes an output unit that outputs content data indicating video content, and a control unit that controls the output unit to cause the output unit to output image data instead of or together with the content data when the output unit is outputting the content data, in which the image data is for prompting a user to measure to obtain the body information indicating a body condition of the user using an external apparatus.

The present disclosure can properly prompt a user to measure to obtain body information when the user is watching video content.

BRIEF DESCRIPTION OF DRAWINGS

These and other objects, advantages and features of exemplary embodiments of the present disclosure will become apparent from the following description thereof taken in conjunction with the accompanying drawings that illustrate general and specific exemplary embodiments of the present disclosure.

DETAILED DESCRIPTION OF INVENTION

Hereinafter, embodiments will be specifically described with reference to the drawings. Detailed description more than necessary may be omitted. For example, detailed description of well-known matters and duplicated description of substantially identical configurations may be omitted. This prevents the following description from being unnecessarily redundant, and facilitates understanding by persons skilled in the art.

The inventors will provide the accompanying drawings and the following description for persons skilled in the art to fully understand the present disclosure, and do not intend that these limit the subject matter described in the appended Claims.

Embodiment 1

Hereinafter, Embodiment 1 will be described using FIGS. 1 to 11.

[1-1. Outline]

Figure 1:
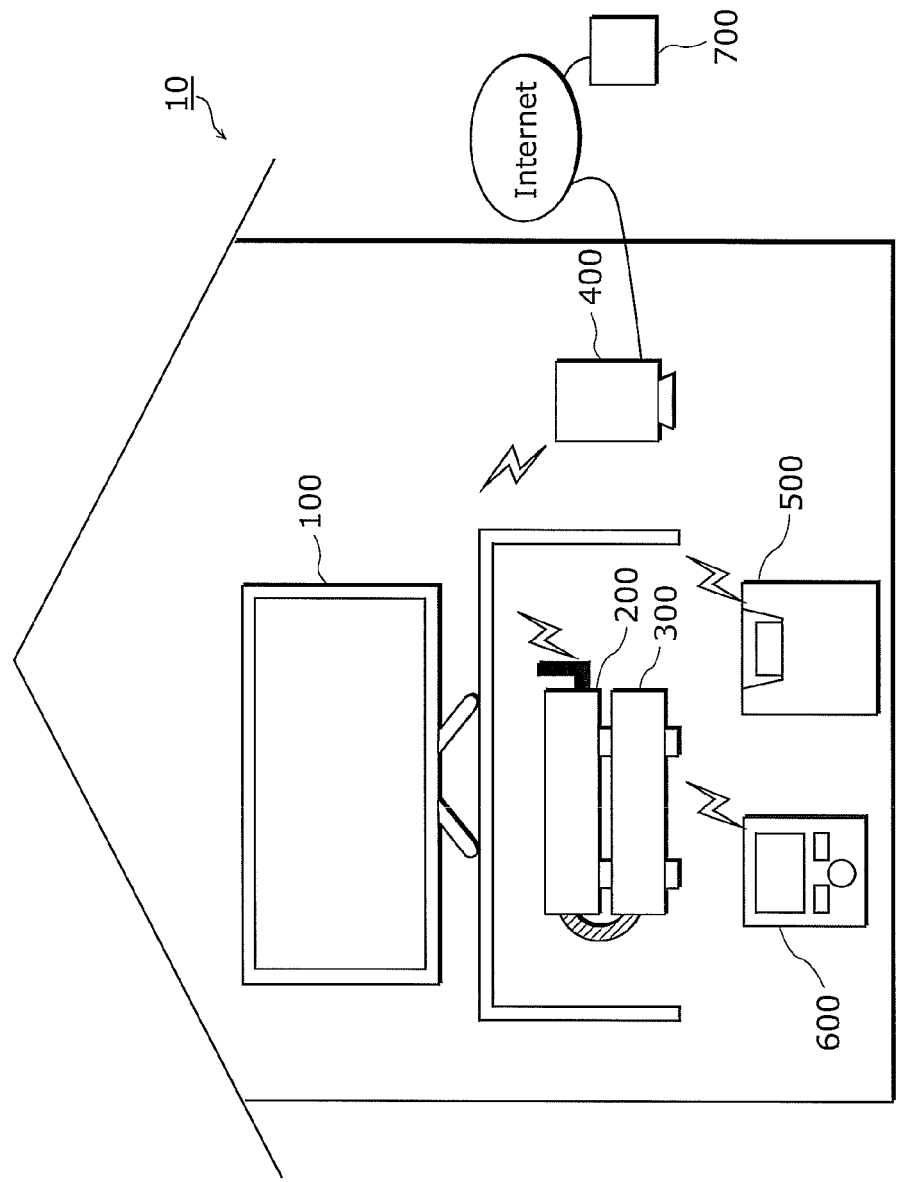
FIG. 1 is a schematic view showing one example of a measurement assistance system according to Embodiment 1.

An outline of an entire system including a gateway 200 according to the present embodiment will be described using FIG. 1. FIG. 1 is a schematic view of one example showing a measurement assistance system 10 according to the present embodiment.

The measurement assistance system 10 according to the present embodiment is a system for assisting a user to measure to obtain body information indicating his or her body condition. Specifically, the measurement assistance system 10 is a system that prompts the user to measure to obtain the body information, generates the result of diagnosis on the body condition of the user, and notifies the user of the result of diagnosis. As shown in FIG. 1, the measurement assistance system 10 includes a television 100, the gateway 200, a set-top box 300, a router 400, a weight scale 500, a sphygmomanometer 600, and a server 700.

The gateway 200 is connected to the set-top box 300 via an audio visual (AV) cable. The set-top box 300 receives cable-casted program content data. The gateway 200 receives the program content data from the set-top box 300 via the AV cable.

The gateway 200 is connected to the television 100 via a high definition multimedia interface (HDMI) cable. The gateway 200 outputs the program content data, which is received from the set-top box 300, to the television 100. The user can watch the program content displayed on the television 100.

The program content means the cablecasted content such as movies, sports programs, and dramas. The program content may include a commercial message (CM).

The gateway 200 is wirelessly connectable to at least one of the weight scale 500 and the sphygmomanometer 600. Specifically, the gateway 200 can communicate with the weight scale 500 and the sphygmomanometer 600 in accordance with the Bluetooth (registered trademark) standard to be wirelessly connected to the weight scale 500 and the sphygmomanometer 600. The Bluetooth is one of short distance wireless communication standards.

The weight scale 500 is an instrument for measuring the weight of a person. The weight scale 500 stores the weight data indicating the weight of the person (user) that performs the measurement. The weight scale 500 can communicate in accordance with the Bluetooth standard.

The sphygmomanometer 600 is an instrument for measuring the blood pressure of a person. The sphygmomanometer 600 stores the blood pressure data indicating the blood pressure of the person (user) that performs the measurement. The sphygmomanometer 600 can communicate in accordance with the Bluetooth standard.

The gateway 200 can receive the weight data from the weight scale 500 or the blood pressure data from the sphygmomanometer 600 as the body information when the gateway 200 is wirelessly connected to the weight scale 500 or the sphygmomanometer 600.

The gateway 200 stores prompting moving picture data that is a moving picture that prompts the user to measure to obtain the body information indicating the body condition such as the weight or the blood pressure. The gateway 200 outputs the prompting moving picture data to the television 100. The user can notice the necessity to measure to obtain the body information when the user sees the prompting moving picture displayed on the television 100.

The gateway 200 is wirelessly connected to the weight scale 500 or the sphygmomanometer 600. In the case where the weight scale 500 stores new weight data and/or in the case where the sphygmomanometer 600 stores new blood pressure data, the gateway 200 receives at least one of the newly stored weight data and blood pressure data from the instrument(s) wirelessly connected to the gateway 200. The gateway 200 transmits at least one of the newly received weight data and blood pressure data to the television 100. The user can check at least one of the values of the weight and blood pressure displayed on the television 100.

The gateway 200 also transmits at least one of the newly received weight data and blood pressure data to the server 700 via the router 400. The server 700 diagnoses the health condition of the user from at least one of the newly received weight data and blood pressure data. Then, the server 700 transmits the diagnosis data via the router 400 to the gateway 200. The gateway 200 transmits the received diagnosis data to the television 100. The user can check the result of diagnosis displayed on the television 100.

Such a system enables the user to manage the health condition of his/her own at home.

Unfortunately, the user is often watching the program content when the user faces the television 100. Accordingly, the problem is how the patient (user) is notified that the patient should measure to obtain the body information while the patient is watching the program content.

The gateway 200 according to the present embodiment includes an HDMI terminal 225 that outputs the program content data indicating program content, and a controller 220. The controller 220 controls the HDMI terminal 225 to cause the HDMI terminal 225 to output the image data instead of or together with the program content data when the program content data is output. The image data is the image data for prompting the user to measure to obtain the body information, which is the information indicating the body condition of the user, using an external apparatus.

Thereby, the gateway 200 can properly prompt the user to measure to obtain the body information while the user is watching the program content. Namely, because the gateway 200 outputs the image data for prompting the user to measure instead of or together with the program content data, the image data disturbs the user's watching the program content. As a result, the user forcibly sees the prompting moving picture instead of watching the program content, or the prompting moving picture together with the program content.

Thereby, the gateway 200 can give a strong impression to the user who is watching the program content, and properly prompt the user to measure to obtain the body information.

[1-2. Electrical Configuration of Gateway]

Figure 2:
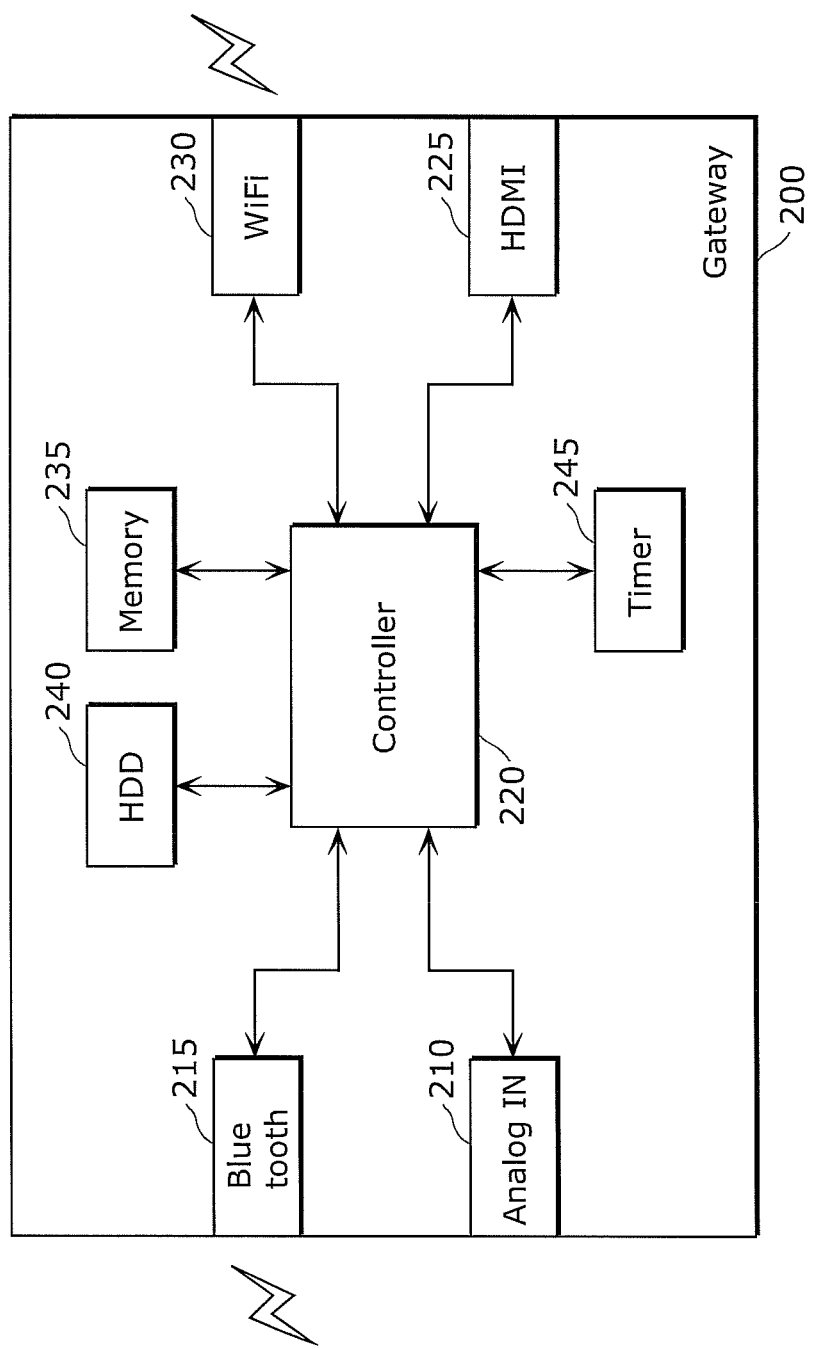
FIG. 2 is a block diagram showing one example of an electrical configuration of a gateway according to Embodiment 1.

Next, the electrical configuration of the gateway 200 will be described using FIG. 2. FIG. 2 is a block diagram showing one example of the electrical configuration of the gateway 200 according to the present embodiment.

The gateway 200 includes an AV cable connection terminal 210, a Bluetooth module 215, the controller 220, the HDMI terminal 225, a wireless local area network (LAN) module 230, a memory 235, a hard disk drive (HDD) 240, and a timer 245.

The controller 220 receives the program content data from the set-top box 300 via the AV cable connection terminal 210. The controller 220 outputs the received program content data to the television 100 via the HDMI terminal 225.

The controller 220 receives at least one of the weight data and blood pressure data from the weight scale 500 and/or the sphygmomanometer 600 via the Bluetooth module 215. The controller 220 outputs at least one of the received weight data and blood pressure data to the television 100 via the HDMI terminal 225. The controller 220 transmits at least one of received weight data and blood pressure data to the server 700 via the wireless LAN module 230.

The controller 220 outputs the prompting moving picture data stored in the HDD 240 to the television 100 via the HDMI terminal 225.

Hereinafter, the configuration of the gateway 200 will be specifically described.

The AV cable connection terminal 210 is one example of an obtaining unit, and is a terminal for connecting the AV cable. The gateway 200 can receive sound data and image data from an external apparatus via the AV cable connection terminal 210. Specifically, the gateway 200 receives the program content data including sound data and image data from the set-top box 300 via the AV cable connection terminal 210.

The Bluetooth module 215 is one example of a receiving unit, and a module for communicating in accordance with the Bluetooth standard. Specifically, the Bluetooth module 215 is a module for receiving the body information obtained by measurement with an external apparatus.

For example, the gateway 200 can receive the data via the Bluetooth module 215 from the external apparatus in accordance with the Bluetooth standard. Specifically, the gateway 200 receives the weight data and blood pressure data from the weight scale 500 and the sphygmomanometer 600 which are examples of the external apparatus (measuring instrument).

The controller 220 is one example of a control unit, and controls the entire gateway 200. Specifically, the controller 220 controls the HDMI terminal 225 to cause the HDMI terminal 225 to output the image data for prompting the user to measure to obtain the body information instead of or together with the program content data when the HDMI terminal 225 is outputting the program content data.

For example, the controller 220 can be implemented with a semiconductor element. The controller 220 may be composed of hardware only, or implemented with a combination of hardware and software. For example, the controller 220 can be implemented with a microcomputer.

The HDMI terminal 225 is one example of an output unit, and a terminal for connecting the HDMI cable. The HDMI terminal 225 functions as an interface for connecting the gateway 200 to an external apparatus such as the television 100. Specifically, the HDMI terminal 225 outputs the program content data indicating the program content.

The wireless LAN module 230 is one example of a communication unit, and a communication module enabling wireless LAN communication. The wireless LAN module 230 is in accordance with the "IEEE 802.11" standard which is an international standard for wireless LAN communication. The wireless LAN module 230 can communicate with the external apparatus and the like via the router 400 by the Internet Protocol (IP). For example, the wireless LAN module 230 is a WiFi module.

The memory 235 is one example of a storage unit, and functions as a work memory for the controller 220. The memory 235 can be implemented with a dynamic random access memory (DRAM) or a ferroelectric memory, for example. The memory 235 stores a control program for controlling the entire gateway 200.

The HDD 240 is one example of a storage unit, which stores the data. The HDD 240 stores the prompting moving picture data for prompting the user to measure to obtain the body information indicating the body condition (such as information on the weight or blood pressure). For example, the prompting moving picture data may be moving picture data transmitted from the server 700 in advance.

The HDD 240 may store the body information in association with time information. Here, the time information is the information indicating the time when the Bluetooth module 215 receives the body information.

The timer 245 is a timer that indicates time. The controller 220 can refer to the timer 245 to recognize the current time.

[1-3. Functional Configuration of Measurement Assistance System]

Figure 3:
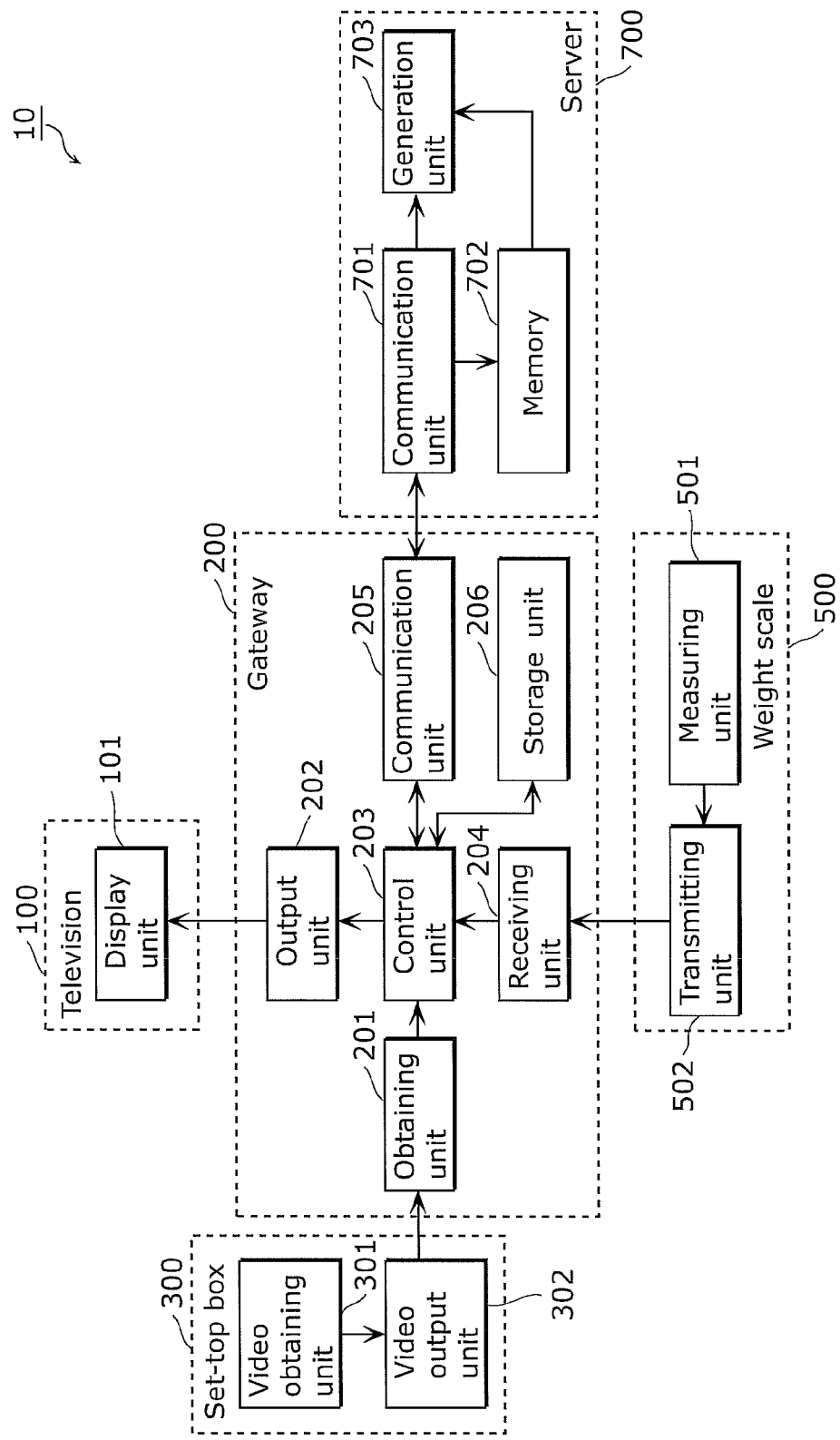
FIG. 3 is a functional block diagram showing one example of the measurement assistance system according to Embodiment 1.

Next, the functional configuration of the measurement assistance system 10 according to the present embodiment will be described using FIG. 3. FIG. 3 is a functional block diagram showing one example of the measurement assistance system 10 according to the present embodiment.

As shown in FIG. 3, the measurement assistance system 10 includes the television 100, the gateway 200, the set-top box 300, the weight scale 500, and the server 700. Here, the weight scale 500 will be described as one example of the measuring instrument, and the same description goes for in the case where the sphygmomanometer 600 or another instrument for measuring the body information is used instead of the weight scale 500.

[1-3-1. Functional Configuration of Television]

The television 100 is one example of an image display apparatus, and includes a display unit 101.

The display unit 101 is a display unit for displaying the program content data, prompting moving picture data, body information, and diagnosis data output from the gateway 200. Specifically, the display unit 101 displays the program content data output from the set-top box 300 via the gateway 200. The display unit 101 displays the body information output from the weight scale 500 via the gateway 200. The display unit 101 displays the prompting moving picture data output from the gateway 200. The display unit 101 displays the diagnosis data output from the server 700 via the gateway 200.

[1-3-2. Functional Configuration of Gateway]

The gateway 200 includes an obtaining unit 201, an output unit 202, a control unit 203, a receiving unit 204, a communication unit 205, and a storage unit 206.

The obtaining unit 201 obtains the program content data from the set-top box 300. The program content data is the content data indicating a broadcasted or cablecasted program and the like.

The output unit 202 outputs the program content data to the television 100.

The control unit 203 controls the output unit 202 to cause the output unit 202 to output the prompting moving picture data instead of or together with the program content data when the output unit 202 is outputting the program content data. For example, the control unit 203 outputs the prompting moving picture data when the output unit 202 is outputting the program content data and the time indicated by the timer 245 matches a predetermined time.

Specifically, when the time indicated by the timer 245 matches the predetermined time and the receiving unit 204 has already received the body information, the control unit 203 controls the output unit 202 to cause the output unit 202 not to output the prompting moving picture data. When the time indicated by the timer 245 matches the predetermined time and the receiving unit 204 has not received the body information yet, the control unit 203 controls the output unit 202 to cause the output unit 202 to output the prompting moving picture data.

In the present embodiment, the predetermined time includes a plurality of times set in advance which is included in the time period during which the user should measure to obtain the body information. Accordingly, when the time indicated by the timer 245 matches one of the plurality of times and the receiving unit 204 has already received the body information, the control unit 203 controls the output unit 202 to cause the output unit 202 not to output the prompting moving picture data. When the time indicated by the timer 245 matches one of the plurality of times and the receiving unit 204 has not received the body information yet, the control unit 203 controls the output unit 202 to cause the output unit 202 to output the prompting moving picture data.

Specifically, the control unit 203 refers to the time information corresponding to the body information stored in the storage unit 206 to determine whether the receiving unit 204 has already received the body information or not. Namely, when the body information corresponding to the time information indicating the time included in the time period during which the user should measure to obtain the body information is stored in the storage unit 206, the control unit 203 controls the output unit 202 to cause the output unit 202 not to output the prompting moving picture data. When the body information corresponding to the time information indicating the time included in the time period during which the user should measure to obtain the body information is not stored in the storage unit 206, the control unit 203 controls the output unit 202 to cause the output unit 202 to output the prompting moving picture data. When no body information is stored in the storage unit 206, the control unit 203 also controls the output unit 202 to cause the output unit 202 to output the prompting moving picture data.

Furthermore, in the case where a predetermined period has passed since the time indicated by the timer 245 matched the latest time of the plurality of times and the receiving unit 204 has not received the body information yet, the control unit 203 controls the communication unit 205 to cause the communication unit 205 to transmit notification data. Here, the notification data is the data indicating that the body information is not received.

The control unit 203 controls the output unit 202 to cause the output unit 202 to output the body information received by the receiving unit 204 to the television 100. The control unit 203 controls the output unit 202 to cause the output unit 202 to output the diagnosis data received by the communication unit 205 to the television 100.

The receiving unit 204 is a receiving unit for receiving the body information obtained by the user by measurement with the weight scale 500.

The communication unit 205 is a first communication unit for transmitting the notification data. Specifically, the communication unit 205 transmits the notification data to the server 700. The communication unit 205 receives the diagnosis data transmitted from the server 700.

The storage unit 206 is a storage unit for storing the body information received by the receiving unit 204. At this time, the storage unit 206 stores the body information in correspondence with the time information.

Specifically, the storage unit 206 stores the body information from a time when the receiving unit 204 receives the body information to a time when the output unit 202 transmits the body information to the television 100 and the communication unit 205 transmits the body information to the server 700. Alternatively, the storage unit 206 stores the body information from a time when the receiving unit 204 receives the body information in the time period during which the user should measure to obtain the body information to a time when the time period will have passed.

[1-3-3. Functional Configuration of Set-Top Box]

The set-top box 300 includes a video obtaining unit 301 and a video output unit 302.

The video obtaining unit 301 is an obtaining unit for obtaining the cablecasted program content data. The video obtaining unit 301 may obtain the program content data through terrestrial broadcasting or satellite-based broadcasting, for example. For example, a cable television tuner is one example of the video obtaining unit 301.

The video output unit 302 outputs the program content data obtained by the video obtaining unit 301 to the gateway 200. For example, an AV output terminal (AV cable connection terminal) is one example of the video output unit 302.

[1-3-4. Functional Configuration of Weight Scale]

The weight scale 500 includes a measuring unit 501 and a transmitting unit 502.

The measuring unit 501 measures to obtain the body information of the user. The body information is the weight, body fat percentage, or basal metabolism rate of the user, for example.

The transmitting unit 502 outputs the body information measured by the measuring unit 501 to the gateway 200. For example, the Bluetooth module is one example of the transmitting unit 502.

The weight scale 500 may include a memory for storing the body information obtained by the measuring unit 501.

[1-3-5. Functional Configuration of Server]

The server 700 is a server apparatus including a communication unit 701, a memory 702, and a generation unit 703.

The communication unit 701 is a second communication unit for receiving the body information transmitted from the gateway 200. The communication unit 701 transmits the diagnosis data generated by the generation unit 703 to the gateway 200. The diagnosis data is the data indicating the health condition of the user. For example, a wireless LAN module or a wired LAN terminal is one example of the communication unit 701.

The memory 702 is a memory for storing the body information received by the communication unit 701. For example, the memory 702 stores a plurality of pieces of the body information obtained by measurement at different times. For example, an HDD or a non-volatile memory is one example of the memory 702.

The generation unit 703 generates the diagnosis data based on the body information stored in the memory 702. For example, the generation unit 703 checks the newly received body information against the movements in the past body information to generate the diagnosis data. Alternatively, the generation unit 703 may generate the diagnosis data based on an instruction given by an administrator of the server 700. For example, a controller such as a central processing unit (CPU) or a microcomputer is one example of the generation unit 703.

[1-4. Operation]

Figure 4:
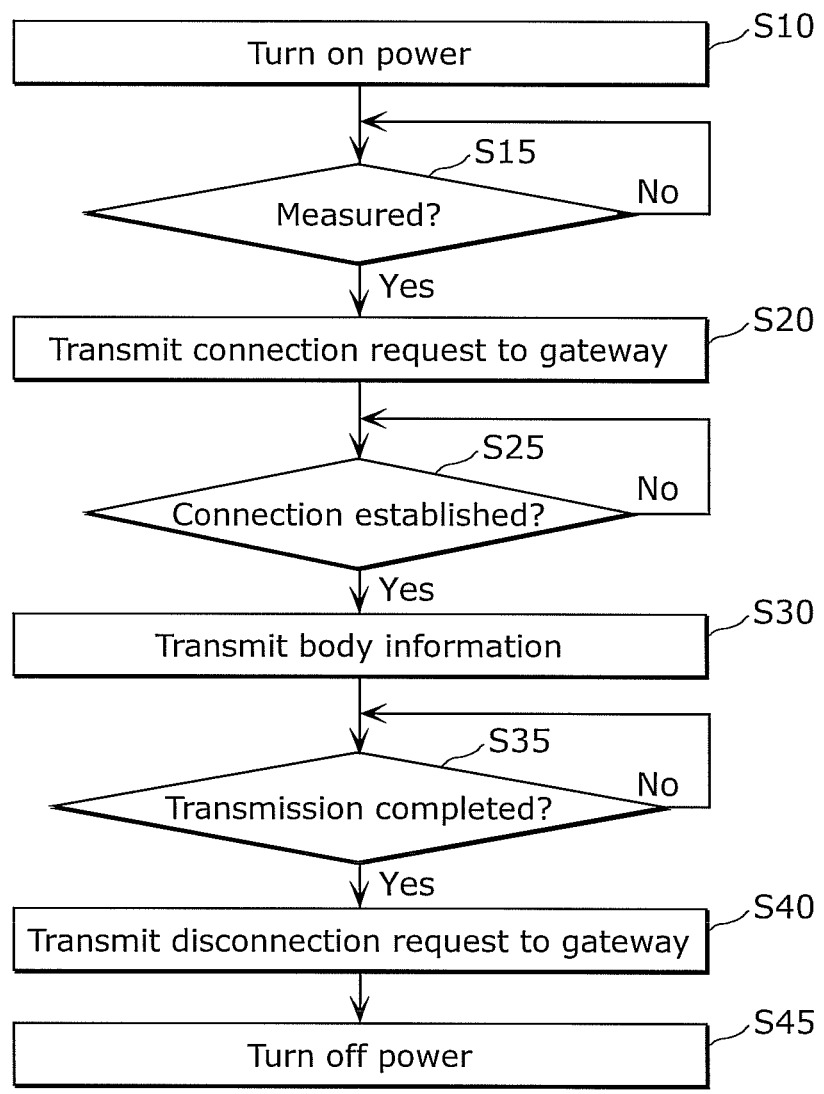
FIG. 4 is a flowchart showing one example of an operation to transmit body information by a measuring instrument according to Embodiment 1.

Next, the operation of at least one of the weight scale 500 and the sphygmomanometer 600 (hereinafter referred to as a measuring instrument) will be described using FIG. 4. The operation of the gateway 200 will be described using FIGS. 5 to 9.

[1-4-1. Operation to Transmit Body Information by Measuring Instrument]

The operation to transmit the body information to the gateway 200 by the measuring instrument will be described using FIG. 4. FIG. 4 is a flowchart showing one example of the operation to transmit the body information by the measuring instrument according to the present embodiment.

First, the user turns on the measuring instrument (S10). The controller in the measuring instrument (such as the measuring unit 501) determines whether the user measured at least one of the weight and the blood pressure (hereinafter referred to as the body information) (S15). When it is determined that the body information is not obtained by measurement (No in S15), a controller in the measuring instrument waits until the body information is obtained by measurement.

When it is determined that the body information is obtained by measurement (Yes in S15), the controller in the measuring instrument stores the obtained body information in the memory in the measuring instrument. Then, the controller in the measuring instrument controls the Bluetooth module in the measuring instrument (such as the transmitting unit 502) to cause the Bluetooth module to transmit a connection request to the gateway 200 (S20). After the controller in the measuring instrument controls the Bluetooth module in the measuring instrument to cause the Bluetooth module to transmit a connection request to the gateway 200, the controller in the measuring instrument determines whether communication is established between the gateway 200 and the measuring instrument in accordance with the Bluetooth standard (S25). When it is determined that the communication is not established (No in S25), the controller in the measuring instrument waits until the communication is established.

When it is determined that the communication is established (Yes in S25), the controller in the measuring instrument controls the Bluetooth module in the measuring instrument to transmit the obtained body information to the gateway 200 (S30). After the transmission of the body information is started, the controller in the measuring instrument determines whether the transmission of the body information is completed or not (S35). When it is determined that the transmission is not completed (No in S35), the controller in the measuring instrument waits until the transmission is completed.

When it is determined that the transmission of the body information is completed (Yes in S35), the controller in the measuring instrument controls the Bluetooth module in the measuring instrument to cause the Bluetooth module to transmit a disconnection request to the gateway 200 (S40). After the Bluetooth is disconnected from the gateway 200, the controller in the measuring instrument turns off the measuring instrument (S45).

[1-4-2. Operation to Upload Body Information to Server by Gateway]

Figure 5:
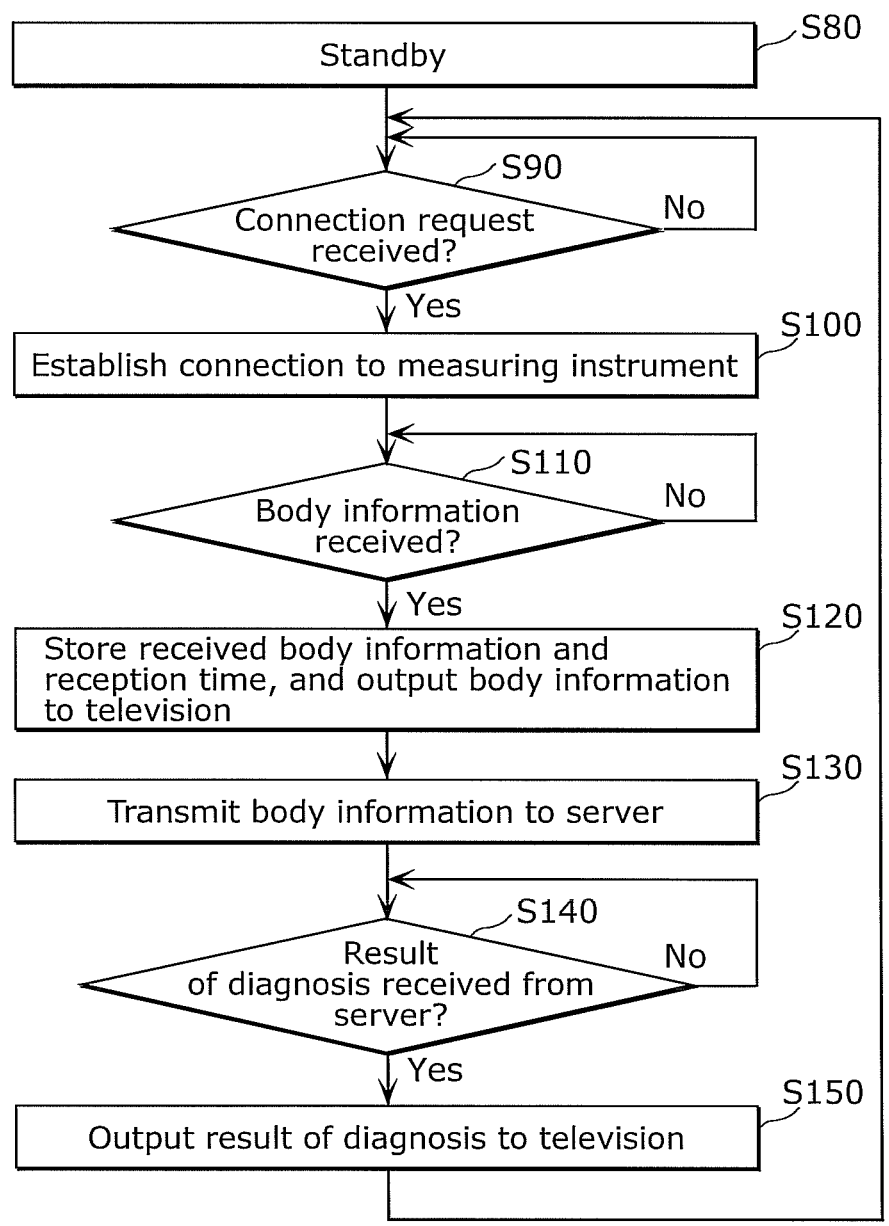
FIG. 5 is a flowchart showing one example of an operation to upload the body information to a server by the gateway according to Embodiment 1.
Figure 6:
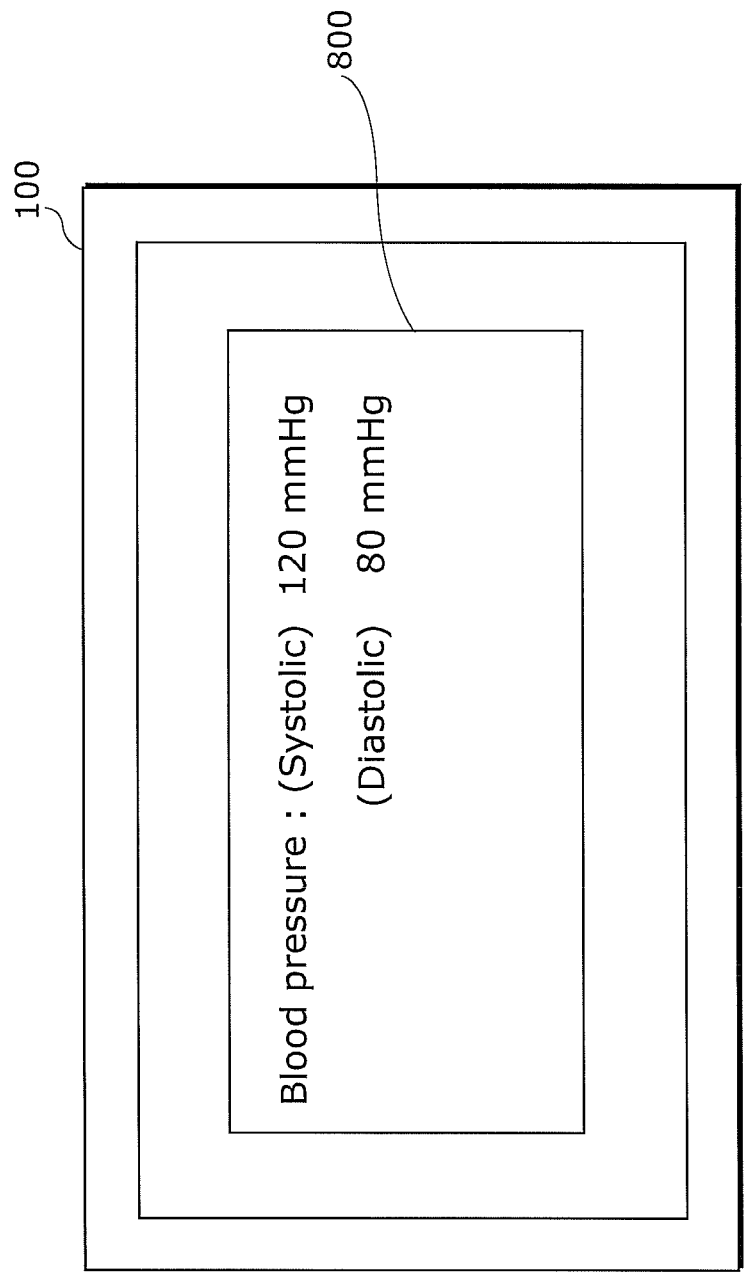
FIG. 6 is a diagram showing one example of a screen that displays the obtained body information according to Embodiment 1.
Figure 7:
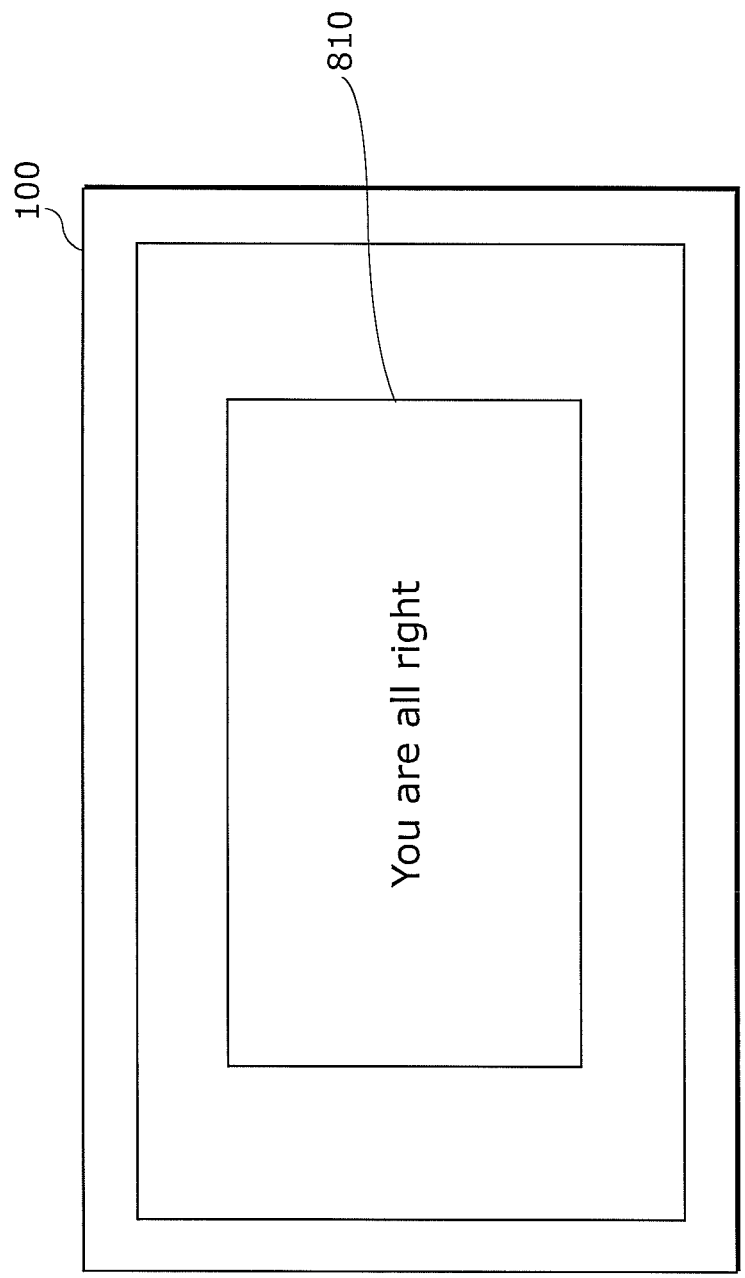
FIG. 7 is a diagram showing one example of a screen that displays a result of diagnosis based on the body information according to Embodiment 1.
Figure 8:
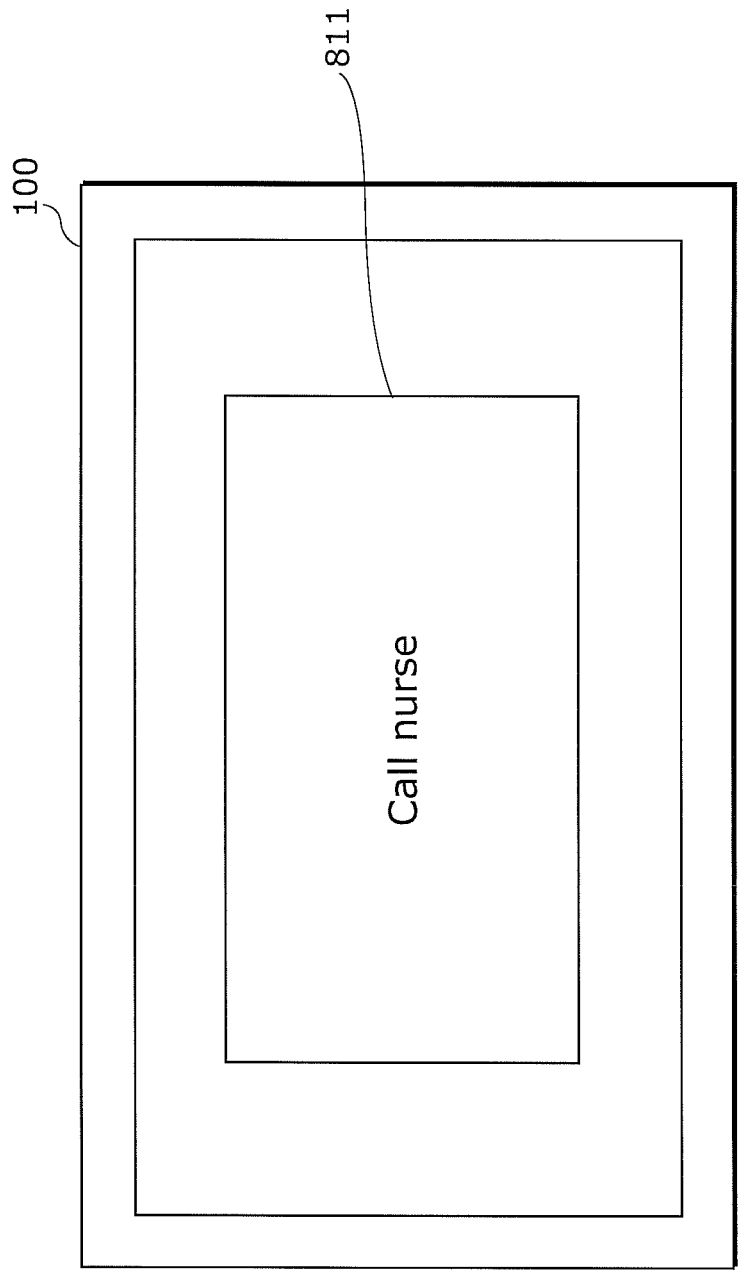
FIG. 8 is a diagram showing another example of the screen that displays a result of diagnosis based on the body information according to Embodiment 1.

The operation to upload the body information received from the measuring instrument to the server 700 by the gateway 200 will be described using FIGS. 5 to 8. FIG. 5 is a flowchart showing one example of an operation to upload the body information to the server 700 by the gateway 200 according to the present embodiment. FIG. 6 is a diagram showing one example of a screen that displays the obtained body information according to the present embodiment. FIG. 7 is a diagram showing one example of a screen that displays a result of diagnosis received from the server 700 according to the present embodiment, in which the user has no problem in the health condition. FIG. 8 is a diagram showing one example of the screen that displays a result of diagnosis received from server 700 according to the present embodiment, in which the user has a problem in the health condition.

In the standby state (S80), the gateway 200 waits until the gateway receives a connection request of the communication in accordance with the Bluetooth standard from the measuring instrument (No in S90). When the gateway 200 receives the connection request (Yes in S90), the gateway 200 establishes the communication with the measuring instrument in accordance with the Bluetooth standard (S100). After the communication is established, the gateway 200 waits until the gateway 200 receives the body information from the measuring instrument (No in S110).

When the gateway 200 receives the body information from the measuring instrument (Yes in S110), the controller 220 stores the received body information in the HDD 240 in correspondence with the time information indicating the time when the gateway 200 receives the body information (S120). The controller 220 outputs the received body information to the television 100 via the HDMI terminal 225 (S120). Thereby, for example, the television 100 displays the screen presenting the body information 800 as shown in FIG. 5. FIG. 5 shows one example in which the gateway 200 receives the blood pressure data as the body information.

After the controller 220 outputs the body information to the television 100, the controller 220 transmits the received body information to the server 700 via the wireless LAN module 230 in correspondence with the time information indicating the date and time when the body information is received (S130). The output of the body information to the television 100 (S120) and the transmission of the body information to the server 700 (S130) may be performed simultaneously, or one of these may be performed prior to the other.

The server 700 manages the body information transmitted from the gateway 200. The server 700 checks the newly received body information against the movements in the past body information transmitted from the gateway 200 so far to diagnose the health condition of the person to which the received body information is attributed. The server 700 transmits the diagnosis data indicating the result of diagnosis to the gateway 200 via the wireless LAN module 230.

After the controller 220 transmits the body information to the server 700, the controller 220 waits until the controller 220 receives the diagnosis data from the server 700 (No in S140). When the controller 220 receives the diagnosis data from the server 700 (Yes in S140), the controller 220 outputs the diagnosis data to the television 100 via the HDMI terminal 225 (S150). For example, when the controller 220 receives the diagnosis data indicating that the user has no problem in the health condition, the result of diagnosis 810 is displayed on the television 100 to tell the user that the user has no problem in the health condition, as shown in FIG. 7.

When the controller 220 receives the diagnosis data indicating that the user has a problem in the health condition, the result of diagnosis 811 is displayed on the television 100 to prompt the user to call a nurse, as shown in FIG. 8. The diagnosis data is one example of the data telling the user what to do when the user has a problem in the health condition. The diagnosis data may be the data for only telling that the user has a problem such as "There is a concern in the health condition."

Thereby, the gateway 200 can upload the body information of the user to the server 700, receive the diagnosis data from the server 700, and output the diagnosis data to the television 100.

[1-4-3. Operation to Output Program Content Data to Television by Gateway]

Figure 9:
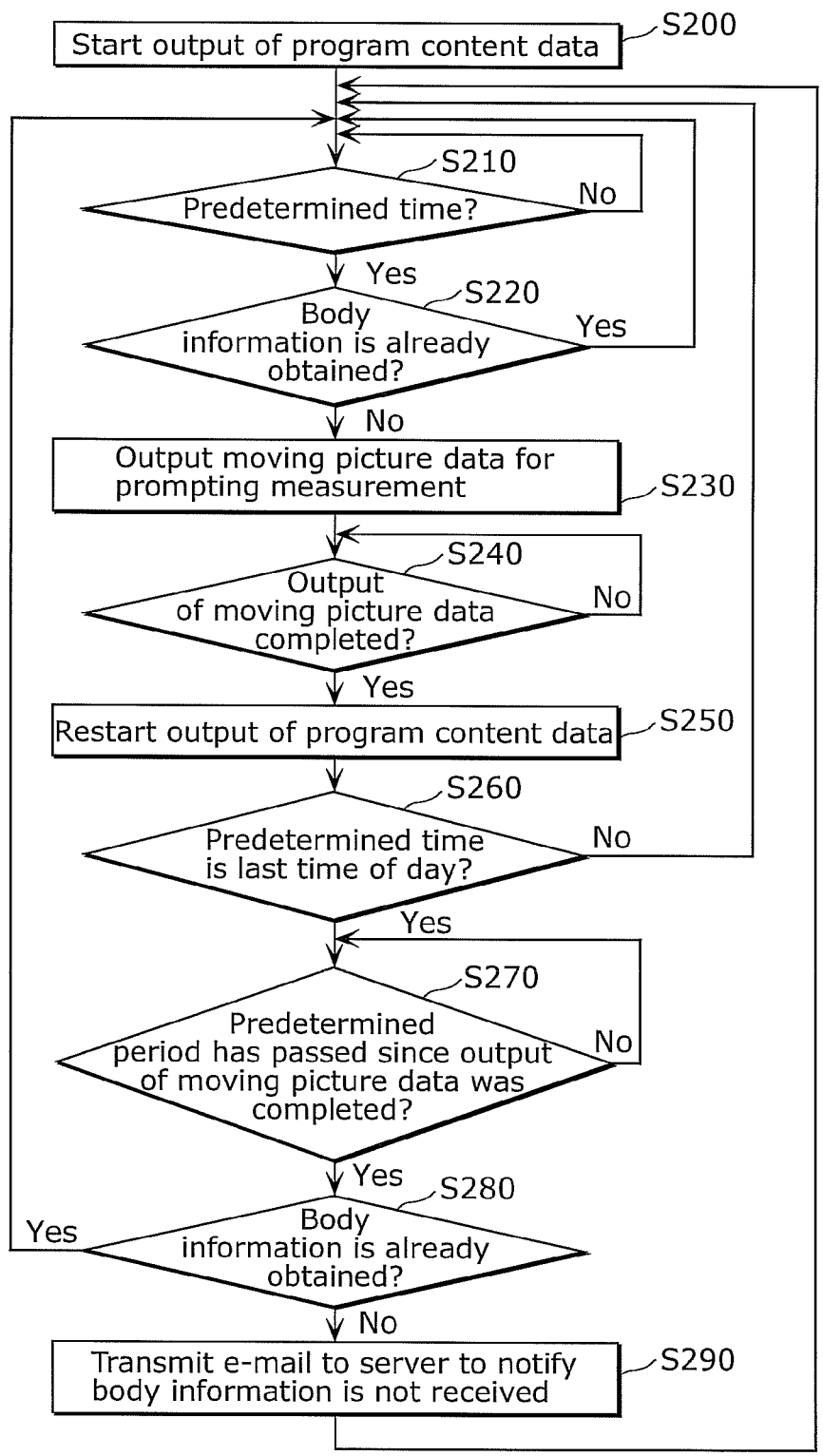
FIG. 9 is a flowchart showing one example of an output operation to a television by the gateway according to Embodiment 1.
Figure 10:
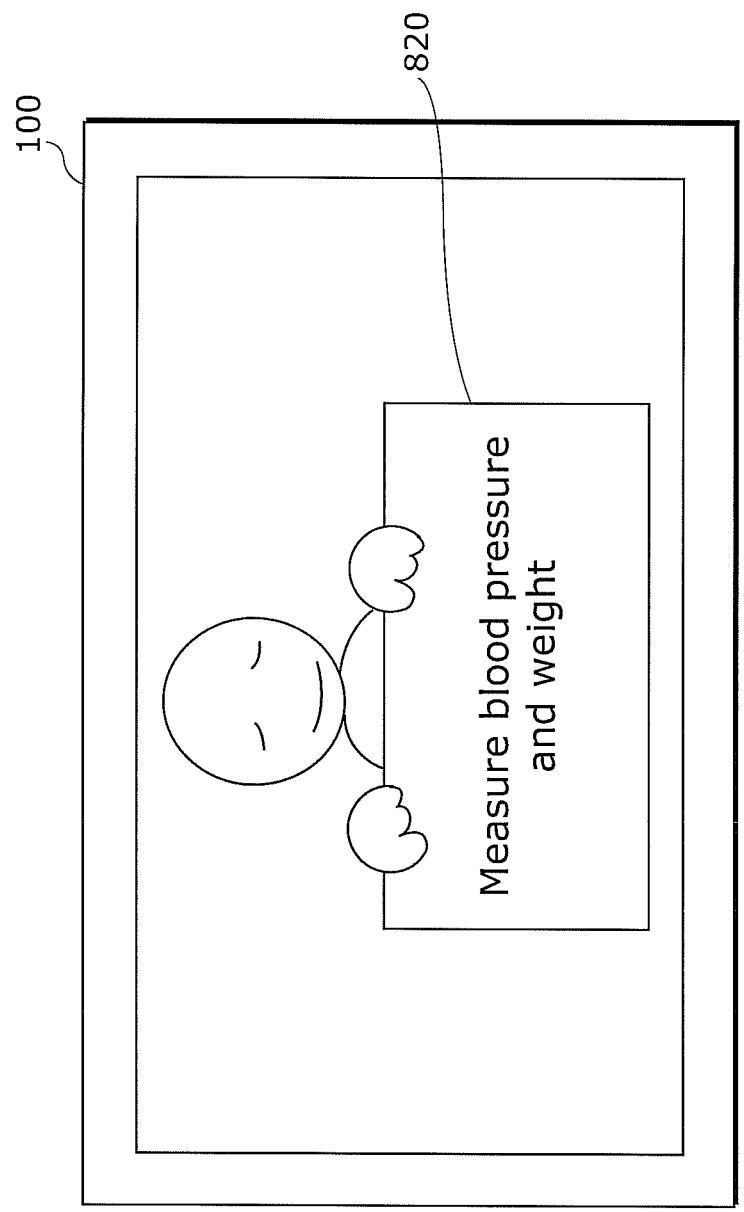
FIG. 10 is a diagram showing one example of a screen that prompts a user to measure to obtain the body information according to Embodiment 1.
Figure 11:
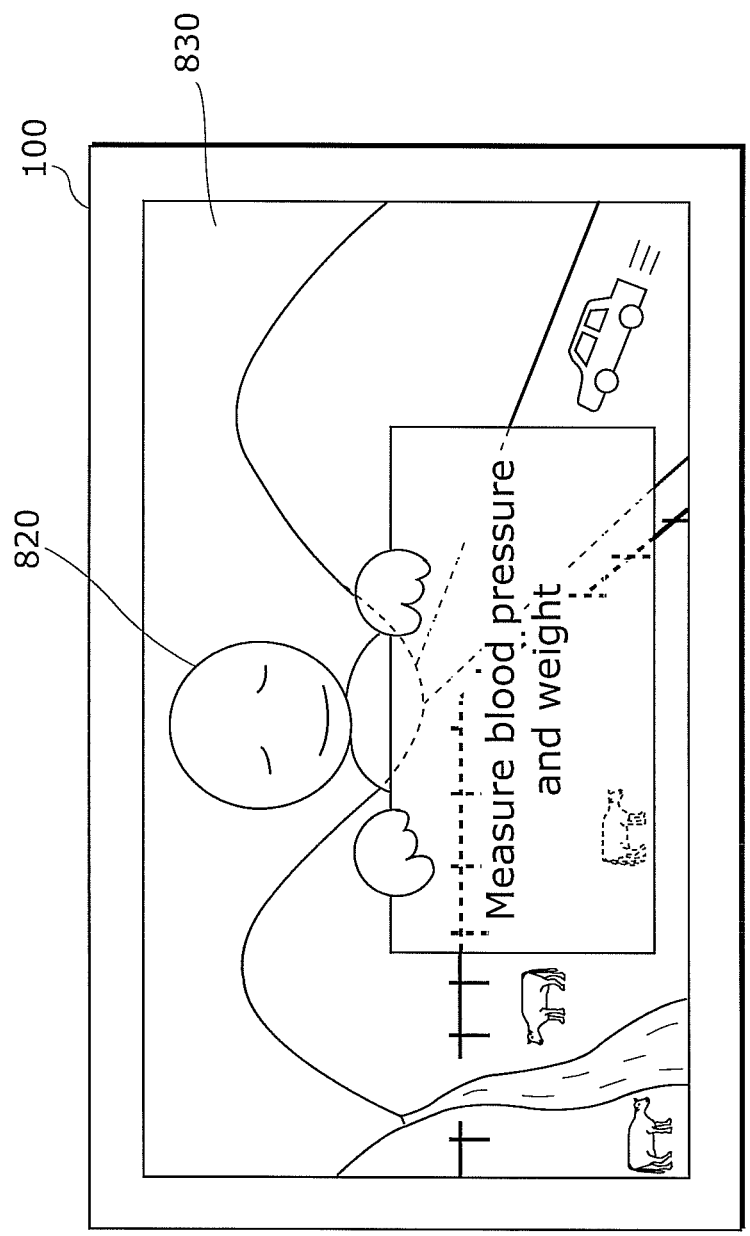
FIG. 11 is a diagram showing another example of the screen that prompts the user to measure to obtain the body information according to Embodiment 1.

Next, the operation when the gateway 200 outputs the program content data received from the set-top box 300 to the television 100 will be described using FIGS. 9 to 11. FIG. 9 is a flowchart showing one example of an output operation to the television 100 by the gateway 200 according to the present embodiment. FIGS. 10 and 11 are diagrams showing examples of the prompting moving picture for prompting the user to measure to obtain the body information according to the present embodiment 1.

In the present embodiment, the user can set a plurality of times in the gateway 200 for a time period during which the user should measure to obtain the body information. The plurality of times set is stored in the memory 235 or in the HDD 240.

For example, assume a case where the time period during which the user should measure to obtain the body information is 6:00 to 20:00. Namely, when the user may measure to obtain the body information once a day during 6:00 to 20:00, the operation will be as follows. At this time, the user can set three times included in the period from 6:00 to 20:00 in the gateway 200, for example. Hereinafter, assume that the user sets 7:00, 12:00, and 17:00 of a day as the plurality of times in the gateway 200.

When the gateway 200 receives the cablecasted program data from the set-top box 300, the gateway 200 starts to output the received program content data to the television 100 (S200). After the gateway 200 starts to output the received program content data to the television 100, the controller 220 refers to the timer 245 to determine whether the predetermined time has come (S210). Namely, the controller 220 determines whether the time indicated by the timer 245 matches the predetermined time. In the present embodiment, the plurality of times is set as the predetermined time, and the controller 220 determines whether the time indicated by the timer 245 matches one of the plurality of times. Specifically, the controller 220 determines whether one of the times 7:00, 12:00, or 17:00 has come. The controller 220 waits until the time indicated by the timer 245 matches the predetermined time (one of the plurality of times) (No in S210).

When the controller 220 determines that the predetermined time has come (Yes in S210), the controller 220 accesses to the HDD 240, and determines whether the body information obtained in the time period of the same day during which the user should measure is stored in the HDD 240 (S220). Specifically, the controller 220 refers to the time information in correspondence with the latest body information stored in the HDD 240 to determine whether the body information is already obtained in the time period of the same day during which the user should measure. When the controller 220 determines that the body information is already stored (Yes in S220), the controller 220 waits until the time indicated by the timer 245 matches the predetermined time again.

When the controller 220 determines that the body information to be obtained in the time period of the same day during which the user should measure is not already stored (No in S220), the controller 220 reads the prompting moving picture data stored in the HDD 240, and outputs the prompting moving picture data to the television 100 via the HDMI terminal 225 (S230). Specifically, the controller 220 interrupts the output of the program content data input from the AV cable connection terminal 210, and outputs the prompting moving picture data from the HDMI terminal 225.

Here, the prompting moving picture data is the moving picture data including a prompting moving picture 820 as shown in FIG. 10. The prompting moving picture data is the image data for prompting the user to measure to obtain the body information indicating the body condition. For example, the prompting moving picture data includes the moving picture data including a text "Measure blood pressure" and the sound data corresponding to "Measure blood pressure." For example, the prompting moving picture data is the moving picture data presented for a predetermined period such as 10 seconds or one minute.

In the present embodiment, the configuration in which the gateway 200 outputs the prompting moving picture data instead of the program content data has been described. However, the configuration of the gateway 200 is not limited to such a configuration. For example, the gateway 200 may be configured to simultaneously output a prompting moving picture 820 smaller than the picture of the program content 830 while the program content data is being output, as shown in FIG. 11. Namely, the gateway 200 may be configured to output the prompting moving picture 820 by superimposing the prompting moving picture 820 on the program content 830. In this case, the gateway 200 may mute the sound of the program content data, and output the sound data included in the prompting moving picture data.

After the controller 220 starts to output the prompting moving picture data, the controller 220 determines whether the output of the prompting moving picture data is completed (S240). When the output of the prompting moving picture data is not completed (No in S240), the controller 220 waits for completion of the output. When the controller 220 determines that the output of the prompting moving picture data is completed (Yes in S240), the controller 220 restarts to output the program content data received from the set-top box 300 (S250).

After the controller 220 restarts the output of the program content data, the controller 220 determines whether the predetermined time at which the prompting moving picture data was output this time is the latest time of the plurality of times set in advance, which are included in the time period during which the user should measure to obtain the body information (S260). Specifically, the controller 220 determines whether the predetermined time at which the prompting moving picture data was output this time is the last time of the day, that is, 17:00. When the controller 220 determines that it is not the last time of the day (No in S260), the controller 220 waits for another predetermined time. Namely, the controller 220 waits until the time indicated by the timer 245 matches the predetermined time again.

When the controller 220 determines that it is the last time of the day (Yes in S260), the controller 220 determines whether a predetermined period has passed since the output of the prompting moving picture data was completed (S270). For example, the controller 220 determines whether 30 minutes have passed since the output of the prompting moving picture data was completed. When the predetermined period has not passed yet (No in S270), the controller 220 waits until the predetermined period passes.

When the controller 220 determines that the predetermined period has passed (Yes in S270), the controller 220 accesses to the HDD 240, and determines whether the body information to be obtained in the time period of the same day during which the user should measure is stored in the HDD 240

(S280). When the controller 220 determines that the body information to be obtained in the time period of the same day during which the user should measure is stored (Yes in S280), the controller 220 waits for the predetermined time of another day.

When the controller 220 determines that the body information to be obtained in the time period of the same day during which the user should measure is not stored (No in S280), the controller 220 transmits the notification data indicating that the body information is not received, namely, the data for notifying that the body information is not received. For example, the notification data is an e-mail indicating that the body information is not received.

Specifically, the controller 220 transmits an e-mail, which indicates that the body information cannot be received from the user, to the server 700 via the wireless LAN module 230. For example, when the server 700 receives the e-mail, the server 700 forwards the e-mail to the doctor or nurse. Thereby, the doctor or nurse can notice that the user does not properly measure to obtain the body information, and through a telephone, for example, encourage the user to obtain the body information.

[1-5. Effects and Others]

Thus, the gateway 200 according to the present embodiment includes the HDMI terminal 225 that outputs the program content data indicating the program content, and the controller 220 that controls the HDMI terminal 225 to cause the HDMI terminal 225 to output the prompting image data for prompting the user to measure to obtain the body information indicating the body condition of the user using the measuring instrument instead of or together with the program content data when the HDMI terminal 225 is outputting the program content data.

Thus, the gateway 200 outputs the prompting moving picture data instead of or together with the program content data when the program content data is being output. This disturbs the user's watching the program content. As a result, the gateway 200 can present the prompting moving picture data and give a strong impression to the viewer who is watching the program content. Thereby, the gateway 200 can properly prompt the user to measure to obtain the body information when the user is watching the program content.

The gateway 200 according to the present embodiment further includes the timer 245 indicating a time. The controller 220 controls the HDMI terminal 225 to cause the HDMI terminal 225 to output the prompting moving picture data instead of or together with the program content data when the HDMI terminal 225 is outputting the program content data and the time indicated by the timer 245 matches a predetermined time.

Thus, the gateway 200 outputs the prompting moving picture data using the time as a trigger. For example, a time suitable for measurement or a time when the user will be watching the program content is set as the predetermined time in advance. Thereby, the prompting moving picture data can be output at a suitable time. As a result, at the suitable time, the gateway 200 can prompt the user to measure to obtain the body information when the user is watching the program content.

The gateway 200 according to the present embodiment further includes the Bluetooth module 215 that receives the body information from the weight scale 500 or the sphygmomanometer 600. The controller 220 controls the HDMI terminal 225 as follows: when the time indicated by the timer 245 matches the predetermined time, the HDMI terminal 225 (i) does not output the prompting moving picture data when the Bluetooth module 215 has already received the body information, and (ii) outputs the prompting moving picture data when the Bluetooth module 215 has not received the body information yet.

Thus, the gateway 200 does not output the prompting moving picture data when the Bluetooth module 215 has already received the body information. Namely, when the user has already measured to obtain the body information, no prompting moving picture is displayed on the television while the user is watching the program content. In other words, the user's watching the program content can be disturbed only when necessary, and the user can receive the prompting.

In the gateway 200 according to the present embodiment, the predetermined time includes a plurality of times set in advance, which is included in the time period during which the user should measure to obtain the body information. The controller 220 controls the HDMI terminal 225 as follows: when the time indicated by the timer 245 matches one of the plurality of times, the HDMI terminal 225 (i) does not output the prompting moving picture data when the Bluetooth module 215 has already received the body information at the time included in the time period, and (ii) outputs the prompting moving picture data when the Bluetooth module 215 has not received the body information at the time included in the time period.

Thus, the gateway 200 does not output the prompting moving picture data when the user has already measured in the time period during which the user should measure to obtain the body information. When the user has not measured yet, the gateway 200 outputs the prompting moving picture data. As a result, the user's watching the program can be disturbed and the user can receive the prompting only when necessary.

The gateway 200 according to the present embodiment further includes the wireless LAN module 230 for transmitting the notification data indicating that the body information is not received. The controller 220 controls the wireless LAN module 230 to cause the wireless LAN module 230 to transmit the notification data when the predetermined has passed since the time indicated by the timer 245 matched the latest time of the plurality of times and the Bluetooth module 215 has not received the body information yet.

Thus, when the user has not measured in the time period during which the user should measure to obtain the body information, the gateway 200 can transmit an e-mail to the server 700 to notify that the body information is not received. As a result, the doctor or others can receive the e-mail transmitted from the server 700 to notice an unusual state of the user.

The gateway 200 according to the present embodiment further includes the HDD 240 for storing the body information received by the Bluetooth module 215. The controller 220 further stores the time information, which indicates the time at which the Bluetooth module 215 receives the body information, in the HDD 240 in correspondence with the body information. The controller 220 controls the HDMI terminal 225 as follows: when the time indicated by the timer 245 matches one of the plurality of times, the HDMI terminal 225 (i) does not output the prompting moving picture data when the body information in correspondence with the time information indicating the time included in the time period is stored in the HDD 240, and (ii) outputs the prompting moving picture data when the body information in correspondence with the time information indicating the time included in the time period is stored in the HDD 240.

Thus, because the body information is stored in the HDD 240 in correspondence with the time information, it is easy to determine whether the user measures in the time period during which the user should measure to obtain the body information.

Embodiment 2

Hereinafter, Embodiment 2 will be described using FIGS. 12 to 14. A difference between Embodiment 2 and Embodiment 1 is the control program for the gateway stored in the memory 235. Hereinafter, duplicated description of substantially same components will be omitted in some cases for simplification of the description.

[2-1. Electrical Configuration of Gateway]

First, the electrical configuration of a gateway 200a according to the present embodiment will be described using FIG. 12. FIG. 12 is a block diagram showing one example of the electrical configuration of the gateway 200a according to the present embodiment.

Figure 12:
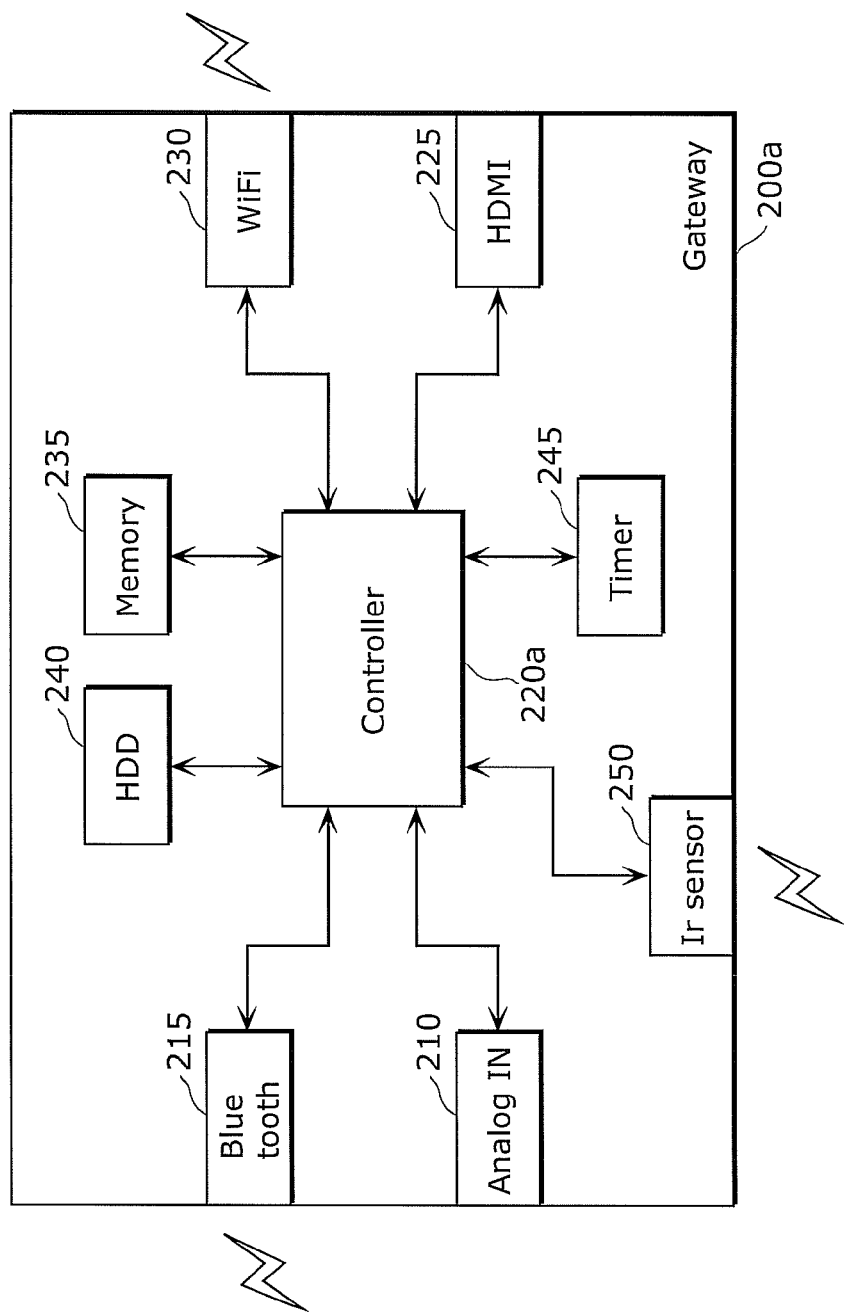
FIG. 12 is a block diagram showing one example of an electrical configuration of a gateway according to Embodiment 2.

As shown in FIG. 12, unlike the gateway 200, the gateway 200a includes a controller 220a instead of the controller 220, and further includes an Ir sensor 250.

The controller 220a has the function of the controller 220. In addition to this, when the time indicated by the timer 245 matches the predetermined time and the Bluetooth module 215 has not received the body information yet, the controller 220a halts execution of the processing based on the instruction accepted by the Ir sensor 250 until the Bluetooth module 215 receives the body information. Specifically, the controller 220a controls the HDMI terminal 225 to cause the HDMI terminal 225 to continuously output the prompting moving picture data in spite of the instruction accepted by the Ir sensor 250. For example, even if an instruction to force termination (turn off) is accepted, the controller 220a does not follow the instruction, and controls the HDMI terminal 225 to cause the HDMI terminal 225 to continuously output the prompting moving picture data.

The controller 220a has the same physical configuration as that of the controller 220. The control program stored in the memory 235 is different from that in Embodiment 1. The controller 220a can read and execute the control program to perform the control described above.

The Ir sensor 250 is one example of an acceptance unit, which is an infrared sensor that accepts an instruction from the user. For example, the Ir sensor 250 accepts a predetermined instruction given by the user using a remote control. Here, the predetermined instruction is an instruction not concerned with the measurement for obtaining the body information.

For example, the predetermined instruction is an instruction concerned with the output of the program content data. Specifically, the predetermined instruction is an instruction indicating start, change, or end of the program content data. For example, the predetermined instruction is an instruction to forcefully terminate the gateway 200a, or an instruction to switch the prompting moving picture data to the program content data.

[2-2. Functional Configuration of Measurement Assistance System]

Next, the functional configuration of the measurement assistance system 10a according to the present embodiment will be described using FIG. 13. FIG. 13 is a functional block diagram showing one example of the measurement assistance system 10a according to the present embodiment.

Figure 13:
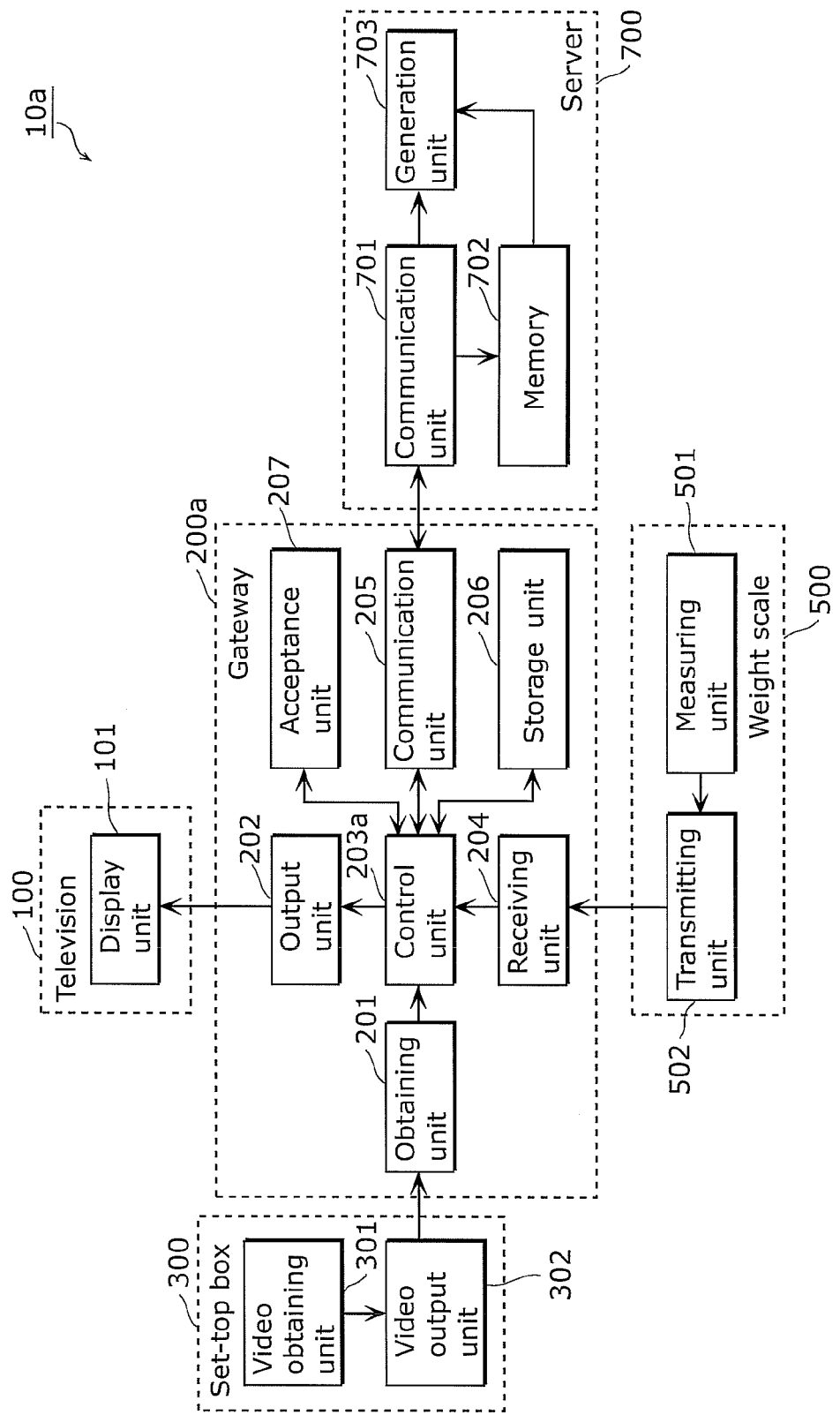
FIG. 13 is a functional block diagram showing one example of a measurement assistance system according to Embodiment 2.
Figure 14:
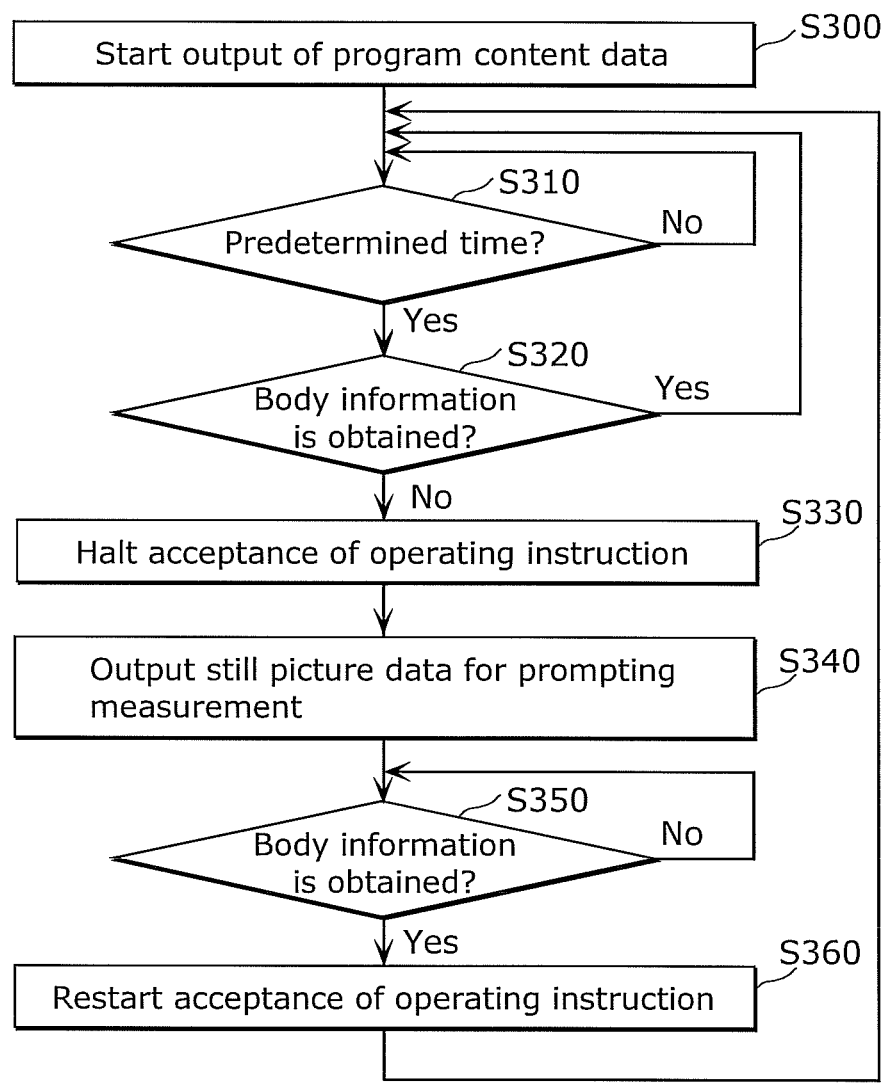
FIG. 14 is a flowchart showing one example of an output operation to a television by a gateway according to Embodiment 2.

As shown in FIG. 13, unlike the measurement assistance system 10, the measurement assistance system 10a includes the gateway 200a instead of the gateway 200. Unlike the gateway 200, the gateway 200a includes a control unit 203a instead of the control unit 203, and further includes an acceptance unit 207.

The control unit 203a has the function of the control unit 203. In addition to this, when the time indicated by the timer 245 matches the predetermined time and the receiving unit 204 has not received the body information yet, the control unit 203a halts execution of the processing based on the instruction accepted by the acceptance unit 207 until the receiving unit 204 receives the body information. Specifically, the control unit 203a controls the output unit 202 that the output unit 202 continuously outputs the prompting moving picture data in spite of the instruction accepted by the acceptance unit 207.

The acceptance unit 207 accepts an instruction from the user. For example, one example of the acceptance unit 207 is the Ir sensor 250 or an operation button provided in the gateway 200a.

[2-3. Operation to Output Program Content Data to Television by Gateway]

The operation to output the program content data to the television 100 by the gateway 200a according to the present embodiment will be described using FIG. 14. FIG. 14 is a flowchart showing one example of the operation to output the program content data to the television 100 by the gateway 200a according to the present embodiment.

When the gateway 200a receives the cablecasted program content data from the set-top box 300, the gateway 200a starts to output the received program content data to the television 100 (S300). After the gateway 200a starts to output the received program content data to the television 100, the controller 220a refers to the timer 245 to determine whether the predetermined time has come (S310). Specifically, the controller 220a determines whether one of the times set in advance by the user, that is, 7:00, 12:00, or 17:00 has come. Also in the present embodiment, similarly to the case of Embodiment 1, assume that 6:00 to 20:00 is set as the time period during which the user should measure to obtain the body information, and 7:00, 12:00, and 17:00 are set as the predetermined times. The controller 220a waits until the time indicated by the timer 245 matches the predetermined time (one of the plurality of times) (No in S310).

When the controller 220a determines that the predetermined time has come (Yes in S310), the controller 220a accesses to the HDD 240, and determines whether the body information to be obtained in the time period of the same day during which the user should measure is stored in the HDD 240 (S320). Specifically, the controller 220a refers to the time information in correspondence with the latest body information stored in the HDD 240 to determine whether the body information to be obtained in the time period of the same day during which the user should measure is already stored. When the controller 220a determines that the body information is already stored (Yes in S320), the controller 220a waits until the time indicated by the timer 245 matches the predetermined time again.

When the controller 220a determines that the body information to be obtained in the time period of the same day during which the user should measure is not stored yet (No in S320), the controller 220a shifts to a state where even if an operating instruction from the user is accepted, the controller 220a does not execute the corresponding operation (S330). For example, the controller 220a does not execute the processing based on the instruction irrelevant to the measurement to obtain the body information.

When the controller 220a shifts to the state where the controller 220a does not execute the corresponding operation even if the operating instruction from the user is accepted, the controller 220a reads prompting still picture data, which is the still picture data for prompting the user to measure to obtain the body information, from the HDD 240, and outputs prompting still picture data to the television 100 via the HDMI terminal 225 (S340).

After the controller 220a outputs the prompting still picture data, the controller 220a waits until the gateway 200a obtains the body information from the measuring instrument (No in S350). During this waiting period, even if the gateway 200a accepts an operating instruction from the user, the gateway 200a does not execute the operation corresponding to the accepted operating instruction. Namely, the gateway 200a neglects the operating instruction from the user.

When the Ir sensor 250 accepts an instruction concerned with the measurement to obtain the body information, the controller 220a may execute the processing based on the instruction. For example, when the Ir sensor 250 accepts an instruction to present a measurement procedure, the controller 220a may control the HDMI terminal 225 to cause the HDMI terminal 225 to output a moving picture that shows the measurement procedure.

When the gateway 200a obtains the body information from the measuring instrument (Yes in S350), the controller 220a again shifts to the state where the controller 220a executes the corresponding operation when an operating instruction from the user is accepted (S360).

[2-4. Effects and Others]

Thus, the gateway 200a according to the present embodiment further includes the Ir sensor 250 that accepts an instruction from the user. When the time indicated by the timer 245 matches the predetermined time and the Bluetooth module 215 has not received the body information yet, the controller 220a halts execution of the processing based on the instruction accepted by the Ir sensor 250 until the Bluetooth module 215 receives the body information.

Thereby, the gateway 200a according to the present embodiment does not operate as intended by the user until the Bluetooth module 215 receives the body information. For example, when the prompting moving picture is displayed on the television 100 and the user gives an instruction to display the program content forcibly, the gateway 200a does not execute the processing based on the instruction. Thus, the operation is not executed as intended by the user until the user measures to obtain the body information. As a result, the user will behave to operate the gateway 200a as intended, improving the probability that the user transmits the body information to the gateway 200a.

In the gateway 200a according to the present embodiment, when the time indicated by the timer 245 matches the predetermined time and the Bluetooth module 215 has not received the body information yet, the controller 220a controls the HDMI terminal 225 to cause the HDMI terminal 225 to continuously output the prompting moving picture data until the Bluetooth module 215 receives the body information.

Thereby, the gateway 200a according to the present embodiment continuously outputs the prompting moving picture data until the Bluetooth module 215 receives the body information. As a result, for example, even if the user operates the set-top box 300, the user cannot cancel the prompting moving picture displayed on the television 100. This situation will continue until the user measures to obtain the body information, consequently improving the possibility that the user measures to obtain the body information.

Other Embodiments

As described above, Embodiments 1 and 2 have been described as examples of the techniques disclosed herein. However, the techniques disclosed in the present disclosure will not be limited to these, and can be applied to embodiments properly modified, replaced, added, or eliminated.

Hereinafter, other embodiments will be described.

In Embodiments 1 and 2, the HDMI terminal 225 has been described as one example of the output unit. The output unit may be configured to output the content data indicating the video content. For example, the output unit may use an AV cable connection terminal or a universal serial bus (USB) terminal.

Here, in Embodiments 1 and 2, the program content has been described as one example of the video content. The program content may be the broadcasted content, the cable-casted content, and the video content delivered through video on demand systems. Alternatively, the video content may be the content recorded on an HDD or a Blu-ray Disc (BD), for example. Namely, the program content data has been described as one example of the content data, but the content data may be any data indicating the content recorded on an HDD or BD.

In Embodiments 1 and 2, the Bluetooth module 215 has been described as one example of the receiving unit. The receiving unit may be configured to receive the body information obtained with the external apparatus. For example, the receiving unit may use a WiFi module, a Near Field Communication (NFC) module, or an infrared sensor. The transmitting unit included in the measuring instrument may have the transmission function corresponding to that of the receiving unit.

In Embodiments 1 and 2, the wireless LAN module 230 has been described as one example of the communication unit (first communication unit). The communication unit may be configured to transmit the notification data indicating that the body information is not received. For example, the communication unit may use a wired LAN terminal or a telephone line connection terminal. The communication unit (second communication unit) included in the server 700 may have the function communicable with the communication unit included in the gateway 200.

In Embodiments 1 and 2, the HDD 240 has been described as one example of the storage unit. The storage unit may be configured to store the body information received by the receiving unit. For example, the storage unit may be a non-volatile memory.

In Embodiment 2, the Ir sensor 250 has been described as one example of the acceptance unit. The acceptance unit may be an operation button provided in the gateway main body. Alternatively, the acceptance unit may be a WiFi module or a Bluetooth module, for example. At this time, the communication unit or the receiving unit may also serve as the acceptance unit.

In Embodiment 2, the configuration of the gateway 200a accepting an instruction from the user has been described. Namely, in Embodiment 2, the configuration of the gateway 200a including the acceptance unit has been described. In contrast, the controller 220a may be configured to neglect the instruction from the user given to the television 100 or the set-top box 300. For example, the controller 220a controls the HDMI terminal 225 to cause the HDMI terminal 225 to continuously output the prompting moving picture data. Thereby, the prompting moving picture is continuously displayed on the television 100 even if the user operates another apparatus.

In Embodiments 1 and 2, the television 100 has been described as one example of the image display apparatus. The image display apparatus is not limited to this, and may be an apparatus for displaying still picture or moving picture data.

For example, the image display apparatus may be a mobile terminal including a display such as mobile terminals.

In Embodiment 1, one day is defined as the time period during which the user should measure to obtain the body information. However, the time period is not limited to this. For example, a plurality of time periods may be provided as the time period. For example, 7:00 to 12:00 and 12:00 to 17:00 may be set as the time periods, and a plurality of times may be set in each of the time periods. In other words, a plurality of times may be set for each of the time periods during which the user should measure to obtain the body information.

In Embodiment 1, the weight scale 500 and the sphygmomanometer 600 have been exemplified as the measuring instrument. However, the measuring instrument is not limited to this. For example, the measuring instrument may be a glucometer or a thermometer. In short, the measuring instrument may be any instrument that can obtain the body information indicating the body condition.

In Embodiment 1, the prompting moving picture data has been exemplified as the image data for prompting the user to measure to obtain the body information that is the information concerned with the body condition. However, the image data is not limited to this. For example, the image data may be the still picture data including text information and prompting the user to measure to obtain the body information. Alternatively, the image data may be the data composed of the still picture data including text information and the sound data. In short, the image data may be any image data for prompting the user to measure to obtain the body information indicating the body condition.

In Embodiment 1, as one example, the gateway is configured to output the prompting moving picture 820 by superimposing the prompting moving picture 820 on the program content 830 when the prompting moving picture data is output together with the program content data. However, the gateway is not limited to such a configuration. For example, the controller 220 may output the program content and the prompting moving picture to the television 100 to be displayed on two separate screens. For example, the controller 220 may output the program content and the prompting moving picture to the television 100 to display the program content on one of the main screen and the sub-screen and display the prompting moving picture on the other thereof.

In Embodiment 1, when the predetermined period has passed since the prompting moving picture data was output at the latest time and the body information has not been received, an e-mail is transmitted to the external server 700. However, the configuration is not limited to this. For example, an alternative may be configured to telephone to the doctor or nurse outside automatically to transmit the sound data indicating an unusual state of the user when the predetermined period has passed since the prompting moving picture data was output at the latest time and the body information has not been received.

In short, the system may be configured to transmit the notification data indicating no reception of the body information to the outside when the predetermined period has passed since the prompting moving picture data was output at the latest time and the body information has not been received.

In Embodiment 1, an example in which the notification data is transmitted after a predetermined period (for example, 30 minutes) has passed since the prompting moving picture data was output has been described. Alternatively, the notification data may be transmitted after a predetermined period has passed since the time indicated by the timer 245 matched the predetermined time.

In Embodiment 2, the configuration in which the time indicated by the timer 245 matches the predetermined time and the Bluetooth module 215 has not received the body information yet, execution of the processing based on the accepted instruction is halted has been described. The timing to halt execution of the processing is not limited to this.

For example, the gateway 200a may be configured to halt execution of the processing based on the accepted instruction when the predetermined period has passed since the prompting moving picture data was output at the latest time of the plurality of times set in advance in the time period in which the user should measure to obtain the body information and the body information has not been received. Namely, the gateway 200a may shift to the state where the gateway 200a does not execute the operation corresponding to the operating instruction even if the gateway 200a accepts the operating instruction from the user. Thus, the user absorbed in watching the television can be more properly prompted to measure to obtain the body information.

In Embodiments 1 and 2, the configuration in which the gateway 200 obtains the program content data from the set-top box 300 has been described. The gateway 200 may have the function of the set-top box 300. For example, the gateway 200 may include a tuner to obtain the program content data through broadcasting or cablecasting.

In other words, the set-top box 300 may have the function of the gateway 200 according to the present disclosure. Namely, the set-top box 300 may be one example of the image output apparatus according to the present disclosure.

In Embodiments 1 and 2, the configuration in which the gateway 200 outputs the program content data to the television 100 has been described. The gateway 200 may have the function of the television 100. For example, the gateway 200 may include a display unit to display the program content data output from the set-top box 300.

In other words, the television 100 may have the function of the gateway 200 according to the present disclosure. Namely, the television 100 may be one example of the image output apparatus according to the present disclosure.

In Embodiments 1 and 2, the configuration in which the gateway 200 includes the control unit that controls the output unit has been described. Alternatively, the gateway 200 may have the output unit, and the server 700 may have the control unit.

Namely, the server 700 may be one example of the image output controller, and may include the control unit that controls the output unit such that instead of or together with the content data, the output unit outputs the image data for prompting the user to measure to obtain the body information indicating the body condition of the user using an external apparatus when the output unit is outputting the content data indicating the video content. Specifically, the controller in the server 700 may control the HDMI terminal 225 in the gateway 200 to switch between the output of the program content data and the output of the prompting moving picture data or simultaneously output the program content data and the prompting moving picture data.

In Embodiments 1 and 2, the configuration of the measurement assistance system 10 including the television 100, the gateway 200, the set-top box 300, the weight scale 500 (and/or the sphygmomanometer 600), and the server 700 has been described. However, the measurement assistance system according to the present disclosure is not limited to this configuration.

For example, the measurement assistance system may not include the set-top box 300. Namely, the measurement assistance system may include the television 100, the gateway 200, the weight scale 500 (and/or the sphygmomanometer 600), and the server 700. For example, the television 100 or the gateway 200 may include a tuner, and obtain the program content data through cablecasting, for example, and output or display the obtained data. Alternatively, the television 100 or the gateway 200 may obtain the video content data recorded in a recording medium such as an HDD, and output or display the obtained data.

The measurement assistance system may not include the server 700. Namely, the measurement assistance system may include the television 100, the gateway 200, and the weight scale 500 (and/or the sphygmomanometer 600). For example, the gateway 200 may store the body information received from the weight scale 500 in the HDD 240, and manage the body information. Such a system enables the user to manage the health condition of his/her own.

As described above, the embodiments have been described as examples of the techniques disclosed in the present disclosure. For this purpose, the accompanying drawings and detailed description have been provided.

Accordingly, the components described in the accompanying drawings and detailed description may include not only components essential to the solution of the problems but also components not essential to that for the purpose of exemplifying the techniques above. It should not be readily determined that these non-essential components are essential only because the non-essential components are described in the accompanying drawings and detailed description.

Moreover, the embodiments described above are intended to exemplify the techniques disclosed in the present disclosure, and various modifications, replacement, addition, elimination, and the like can be made within the scope of the appended Claims and their equivalents.

The present disclosure can be applied to the image output apparatuses such as gateways, recorders, and televisions.

The invention claimed is:

1. An image output apparatus comprising:
an output unit configured to output content data indicating video content; and
a control unit configured to control the output unit to cause the output unit to output image data instead of or together with the content data when the output unit is outputting the content data, the image data being for prompting a user to measure to obtain body information indicating a body condition of the user using an external apparatus;
a receiving unit configured to receive the body information measured using the external apparatus; and
an acceptance unit configured to accept an instruction from the user,
wherein the control unit is further configured to maintain a state where processing based on an instruction accepted by the acceptance unit is not performed, after the output unit outputs the image data until the receiving unit receives the body information, and, after the receiving unit receives the body information, shift to a state where processing based on an instruction accepted by the acceptance unit is allowed to be performed.

2. The image output apparatus according to claim 1, further comprising
a timer that indicates time,
wherein the control unit is configured to control the output unit to cause the output unit to output the image data instead of or together with the content data when the output unit is outputting the content data and the time indicated by the timer matches a predetermined time.

3. The image output apparatus according to claim 2,
wherein when the time indicated by the timer matches the predetermined time, the control unit is configured to control the output unit to cause the output unit (i) not to output the image data when the receiving unit has already received the body information, and (ii) to output the image data when the receiving unit has not received the body information yet.

4. The image output apparatus according to claim 3,
wherein the predetermined time includes a plurality of times set in advance, which are included in a time period during which the user should measure to obtain the body information, and
when the time indicated by the timer matches one of the plurality of times, the control unit is configured to control the output unit to cause the output unit (i) not to output the image data when the receiving unit has already received the body information at the time included in the time period, and (ii) to output the image data when the receiving unit has not received the body information at the time included in the time period.

5. The image output apparatus according to claim 4, further comprising
a communication unit configured to transmit notification data indicating that the body information is not received,
wherein the control unit is further configured to control the communication unit to cause the communication unit to transmit the notification data when a predetermined period has passed since the time indicated by the timer matched the latest time of the plurality of times and the receiving unit has not received the body information yet.

6. The image output apparatus according to claim 4, further comprising
a storage unit configured to store the body information received by the receiving unit,
wherein the control unit is configured to store time information in the storage unit in correspondence with the body information, the time information indicating a time at which the receiving unit receives the body information, and
when the time indicated by the timer matches one of the plurality of times, the control unit is configured to control the output unit to cause the output unit (i) not to output the image data when the body information corresponding to the time information indicating the time included in the time period is stored in the storage unit, and (ii) to output the image data when the body information corresponding to the time included in the time period information is not stored in the storage unit.

7. The image output apparatus according to claim 1,
wherein in the state where processing based on an instruction accepted by the acceptance unit is not performed, the control unit is configured to:
perform processing based on a first instruction concerned with measuring the body information accepted by the acceptance unit if the acceptance unit accepts the first instruction; and
not perform processing based on a second instruction concerned with outputting the content data accepted by the acceptance unit if the acceptance unit accepts the second instruction.

8. The image output apparatus according to claim 3,
wherein the control unit is configured to control the output unit to cause the output unit to continuously output the image data until the receiving unit receives the body information, when the time indicated by the timer matches the predetermined time and the receiving unit has not received the body information yet.

9. A measurement assistance system, comprising:
the image output apparatus according to claim 1;
the external apparatus; and
an image display apparatus,
wherein the external apparatus includes:
- a measuring unit configured to measure to obtain body information indicating a body condition of the user; and
- a transmitting unit configured to transmit the body information obtained by the measuring unit, the control unit is further configured to control the output unit to cause the output unit to output the body information received by the receiving unit, and
the image display apparatus includes a display unit configured to display the content data, image data, and body information that are output from the output unit.

10. The measurement assistance system according to claim 9, further comprising a server apparatus,
wherein the image output apparatus further includes a first communication unit configured to transmit the body information received by the receiving unit to the server apparatus,
the server apparatus includes:
- a second communication unit configured to receive the body information transmitted by the first communication unit;
- a memory that stores the body information received by the second communication unit; and
- a generation unit configured to generate diagnosis data indicating a health condition of the user based on the body information stored in the memory, the second communication unit is further configured to transmit the diagnosis data generated by the generation unit,
the first communication unit is further configured to receive the diagnosis data transmitted by the second communication unit,
the control unit is further configured to control the output unit to cause the output unit to output the diagnosis data received by the first communication unit, and
the display unit is further configured to display the diagnosis data output from the output unit.

11. An image output controller comprising
a control unit configured to control an output unit that outputs content data indicating video content to cause the output unit to output image data instead of or together with the content data when the output unit is outputting the content data, the image data being for prompting a user to measure to obtain body information indicating a body condition of the user using an external apparatus;
a receiving unit configured to receive the body information measured using the external apparatus; and
an acceptance unit configured to accept an instruction from the user,
wherein the control unit is further configured to maintain a state where processing based on an instruction accepted by the acceptance unit is not performed, after the output unit outputs the image data until the receiving unit receives the body information, and, after the receiving unit receives the body information, shift to a state where processing based on an instruction accepted by the acceptance unit is allowed to be performed.

12. An image outputting method comprising:
outputting, by an output unit, content data indicating video content;
causing, by a control unit, the output unit to output image data instead of or together with the content data when the content data is output, the image data being for prompting a user to measure to obtain body information indicating a body condition of the user using an external apparatus;
receiving, by a receiving unit, the body information measured using the external apparatus; and
accepting, by an acceptance unit, an instruction from the user,
wherein a state, where processing based on an instruction accepted by the acceptance unit is not performed, is maintained by the control unit after the image data is output by the output unit until the body information is received by the receiving unit, and, after the body information is received by the receiving unit, the state is shifted, by the control unit, to a state where processing based on an instruction accepted by the acceptance unit is allowed to be performed.

* * * * *